(12) United States Patent
Sakakibara et al.

(10) Patent No.: US 9,335,630 B2
(45) Date of Patent: May 10, 2016

(54) PATTERN-FORMING METHOD, AND RADIATION-SENSITIVE COMPOSITION

(71) Applicant: JSR CORPORATION, Tokyo (JP)

(72) Inventors: Hirokazu Sakakibara, Tokyo (JP); Masafumi Hori, Tokyo (JP); Taiichi Furukawa, Tokyo (JP); Koji Ito, Tokyo (JP)

(73) Assignee: JSR CORPORATION, Tokyo (JP)

( * ) Notice: Subject to any disclaimer, the term of this patent is extended or adjusted under 35 U.S.C. 154(b) by 0 days.

(21) Appl. No.: 14/640,882

(22) Filed: Mar. 6, 2015

(65) Prior Publication Data
US 2015/0177616 A1    Jun. 25, 2015

Related U.S. Application Data

(63) Continuation of application No. 13/866,093, filed on Apr. 19, 2013, now Pat. No. 9,034,559, which is a continuation of application No. PCT/JP2011/073974, filed on Oct. 18, 2011.

(30) Foreign Application Priority Data

Oct. 22, 2010  (JP) ................ 2010-237767

(51) Int. Cl.
| | | |
|---|---|---|
| *G03F 7/004* | (2006.01) | |
| *G03F 7/30* | (2006.01) | |
| *G03F 7/038* | (2006.01) | |
| *C07C 381/12* | (2006.01) | |
| *C08F 220/24* | (2006.01) | |
| *C08F 220/10* | (2006.01) | |
| *G03F 7/027* | (2006.01) | |
| *G03F 7/039* | (2006.01) | |
| *G03F 7/11* | (2006.01) | |
| *G03F 7/20* | (2006.01) | |
| *G03F 7/32* | (2006.01) | |

(52) U.S. Cl.
CPC .............. *G03F 7/038* (2013.01); *C07C 381/12* (2013.01); *C08F 220/10* (2013.01); *C08F 220/24* (2013.01); *G03F 7/0045* (2013.01); *G03F 7/0046* (2013.01); *G03F 7/027* (2013.01); *G03F 7/0397* (2013.01); *G03F 7/11* (2013.01); *G03F 7/2041* (2013.01); *G03F 7/30* (2013.01); *G03F 7/325* (2013.01); *Y10S 430/114* (2013.01); *Y10S 430/115* (2013.01)

(58) Field of Classification Search
CPC ..... G03F 7/0045; G03F 7/0046; G03F 7/027; G03F 7/0397; G03F 7/11; G03F 7/2041; G03F 7/325; C08F 220/10
USPC ........ 430/270.1, 434, 435, 913, 914; 526/287
See application file for complete search history.

(56) References Cited

U.S. PATENT DOCUMENTS

| | | | |
|---|---|---|---|
| 4,910,122 A | 3/1990 | Arnold et al. | |
| 7,569,326 B2 | 8/2009 | Ohsawa et al. | |
| 8,703,401 B2 | 4/2014 | Furukawa et al. | |
| 8,795,954 B2 | 8/2014 | Sakakibara et al. | |
| 8,980,539 B2 | 3/2015 | Furukawa et al. | |
| 2004/0072094 A1 | 4/2004 | Shima et al. | |
| 2006/0234154 A1 | 10/2006 | Nishimura et al. | |
| 2008/0187860 A1 | 8/2008 | Tsubaki et al. | |
| 2009/0269696 A1 | 10/2009 | Ohsawa et al. | |
| 2011/0177462 A1 | 7/2011 | Hatakeyama et al. | |
| 2011/0294069 A1 | 12/2011 | Bae et al. | |
| 2012/0009527 A1 | 1/2012 | Hatakeyama et al. | |
| 2013/0164695 A1 | 6/2013 | Nishimura et al. | |
| 2013/0224661 A1 | 8/2013 | Sakakibara et al. | |
| 2013/0316287 A1 | 11/2013 | Sakakibara et al. | |

(Continued)

FOREIGN PATENT DOCUMENTS

| | | |
|---|---|---|
| JP | 06-012452 B2 | 5/1984 |
| JP | 59-093448 | 5/1984 |

(Continued)

OTHER PUBLICATIONS

Office Action issued Dec. 2, 2014, in Japanese Patent Application No. 2012-538604 (w/ English translation).
Office Action issued Aug. 26, 2014, in Japanese Patent Application No. 2012-537652 (w/ English translation).
Office Action issued Sep. 29, 2014, in U.S. Appl. No. 14/307,296, filed Jun. 17, 2014.
Office Action issued Aug. 5, 2014 in Japanese Patent Application No. 2012-538604 (w/ English translation).
Final Office Action for the U.S. Appl. No. 13/855,749, dated Jun. 2, 2014.
Japanese Office Action for corresponding JP Application No. 2011-043032, Apr. 8, 2014 (w/ English translation).
Office Action with Form PTO-892 Notice of References Cited issued by the U.S. Patent and Trademark Office for the U.S. Appl. No. 13/861,416, Jan. 10, 2014.
Office Action with Form PTO-892 Notice of Reference Cited issued by the U.S. Patent and Trademark Office for the U.S. Appl. No. 13/855,749, Dec. 11, 2013.

(Continued)

*Primary Examiner* — Amanda C Walke
(74) *Attorney, Agent, or Firm* — Oblon, McClelland, Maier & Neustadt, L.L.P

(57) ABSTRACT

A pattern-forming method includes providing a resist film on a substrate using a radiation-sensitive composition. The resist film is exposed. The exposed resist film is developed using a developer solution. The developer solution includes no less than 80% by mass of an organic solvent. The radiation-sensitive composition includes at least two components including a first polymer and a radiation-sensitive acid generator. The first polymer includes a structural unit having an acid-labile group. One or more components of the radiation-sensitive composition have a group represented by a formula (1). $A^-$ represents $-N^--SO_2-R^D$, $-COO^-$, $-O^-$ or $-SO_3^-$. $-SO_3^-$ does not directly bond to a carbon atom having a fluorine atom. $R^D$ represents a linear or branched monovalent hydrocarbon group, or the like. $X^+$ represents an onium cation.

$$-A^- X^+ \quad (1)$$

18 Claims, No Drawings

(56) References Cited

U.S. PATENT DOCUMENTS

| | | |
|---|---|---|
| 2014/0255854 A1 | 9/2014 | Sakakibara et al. |
| 2014/0295350 A1 | 10/2014 | Sakakibara et al. |

FOREIGN PATENT DOCUMENTS

| | | |
|---|---|---|
| JP | 05-188598 | 7/1993 |
| JP | 2000-199953 | 7/2000 |
| JP | 2002-525683 | 8/2002 |
| JP | 2003-043678 A | 2/2003 |
| JP | 3869306 B2 | 5/2003 |
| JP | 2005-352384 | 12/2005 |
| JP | 2008-058538 | 3/2008 |
| JP | 2008-281974 | 11/2008 |
| JP | 2008-292975 | 12/2008 |
| JP | 2009-025707 | 2/2009 |
| JP | 2009-025708 | 2/2009 |
| JP | 2009-025723 | 2/2009 |
| JP | 2009-211051 | 9/2009 |
| JP | 2009-258585 | 11/2009 |
| JP | 2009-258586 | 11/2009 |
| JP | 2010-024330 | 2/2010 |
| JP | 2010-039476 A | 2/2010 |
| JP | 2010-066503 | 3/2010 |
| JP | 2010-096992 A | 4/2010 |
| JP | 2010-128391 A | 6/2010 |
| JP | 2010-139996 | 6/2010 |
| JP | 2010-152349 A | 7/2010 |
| JP | 2010-152353 | 7/2010 |
| JP | 2010-197619 A | 9/2010 |
| JP | 2011-022560 A | 2/2011 |
| JP | 2011-100089 A | 5/2011 |
| JP | 2011-170316 A | 9/2011 |
| JP | 2011-191727 A | 9/2011 |
| JP | 2011-203644 | 10/2011 |
| JP | 2011-209520 A | 10/2011 |
| JP | 2011-221501 A | 11/2011 |
| JP | 2011-221513 | 11/2011 |
| JP | 2012-27438 A | 2/2012 |
| JP | 2012-032780 A | 2/2012 |
| JP | 2012-032806 A | 2/2012 |
| JP | 2012-032807 A | 2/2012 |
| JP | 2012-053307 A | 3/2012 |
| JP | 2012-073565 A | 4/2012 |
| JP | 2012-153874 A | 8/2012 |
| TW | 200839467 A | 10/2008 |
| WO | WO 2004/068242 | 8/2004 |
| WO | WO 2007/116664 | 10/2007 |
| WO | WO 2008/153109 | 12/2008 |
| WO | WO 2008/153110 | 12/2008 |
| WO | WO 2010/007993 | 1/2010 |
| WO | WO 2010/119910 | 10/2010 |

OTHER PUBLICATIONS

International Search Report for corresponding International Application No. PCT/JP2011/073974, Dec. 20, 2011.
Lee et al., "Double exposure technology using silicon containing materials", SPIE, 2006, vol. 6153, pp. 1-7.
Nishikubo et al., "Convenient Syntheses of Cyclic Carbonates by new Reaction of Oxtranes with β-Butyrolactone", Tetrahedron Letters, pp. 3741-3744, vol. 27, No. 32, 1986.
Calo et al., "Cyclic Carbonate Formation from Carbon Dioxide and Oxiranes in Tetrabutylammonium Halides as Solvents and Catalysts", Organic Letters, 2002, pp. 2561-2563, vol. 4, No. 15.
International Search Report for corresponding International Application No. PCT/JP2011/056120, Jun. 7, 2011 (w/ English translation).
International Search Report for corresponding International Application No. PCT/JP2011/070197, Oct. 11, 2011 (w/ English translation).
International Search Report for corresponding International Application No. PCT/JP2011/072296, Oct. 25, 2011 (w/ English translation).
United States Office Action for corresponding U.S. Appl. No. 13/861,416, Sep. 9, 2013.
Office Action issued Mar. 3, 2015 in Japanese Patent Application No. 2012-539740 (with English translation).
Omnova Solutions Inc., "Polyfox", [online] Jun. 2009, [retrieved on Aug. 17, 2015], on the Internet <URL: http://www.omnova.comlproducts/ chemicals/ documents/DiolsBrochure 2009. pdf>, 3 pages.
Office Action issued May 12, 2015 in Taiwanese Patent Application No. 100137128 (with English translation).
Combined Office Action and Search Report issued May 21, 2015 in Taiwanese Patent Application No. 100138099 (with English language translation).
Office Action issued Jan. 12, 2016, in Japanese Patent Application No. 2015-035925 (w/ English translation).
Office Action issued Jan. 12, 2016, in Japanese Patent Application No. 2015-086647 (w/ English translation).
Office Action issued Jan. 26, 2016, in Japanese Patent Application No. 2012-538604 (w/ English translation).
Office Action issued Mar. 22, 2016, in Japanese Patent Application No. JP 2012-539740 (w/ English translation).

PATTERN-FORMING METHOD, AND RADIATION-SENSITIVE COMPOSITION

CROSS-REFERENCE TO RELATED APPLICATIONS

The present application is a continuation application of U.S. patent application Ser. No. 13/866,093 filed Apr. 19, 2013, which in turn is a continuation application of International Application No. PCT/JP2011/073974, filed Oct. 18, 2011, which claims priority to Japanese Patent Application No. 2010-237767, filed Oct. 22, 2010. The contents of these applications are incorporated herein by reference in their entirety.

BACKGROUND OF THE INVENTION

1. Field of the Invention

The present invention relates to a pattern-forming method, and a radiation-sensitive composition.

2. Discussion of the Background

Chemically amplified type radiation-sensitive compositions for use in microfabrication by lithography generate an acid upon irradiation with a visible light, ultraviolet rays, etc., at light-exposed sites, and a chemical reaction that proceeds with the acid that serves as a catalyst allows the difference in dissolution rates in developer solutions to be produced between the light-exposed sites and light-unexposed sites, thereby enabling resist patterns to be formed on the substrate.

On the other hand, in a known technique for improving resolving power using characteristic features of such radiation-sensitive compositions without increasing the number of steps using a preexisting apparatus, an organic solvent having lower polarity than that of aqueous alkali solutions is used as a developer solution (see Japanese Unexamined Patent Application, Publication No. 2000-199953). This technique utilizes a possible increase of an optical contrast in the case in which an organic solvent is used, whereby formation of a fine pattern is enabled, contrary to the case in which an aqueous alkali solution is used as a developer solution for forming a trench pattern or hole pattern, accompanied by a poor optical contrast leading to a difficulty in formation of a fine pattern.

SUMMARY OF THE INVENTION

According to one aspect of the present invention, a pattern-forming method includes providing a resist film on a substrate using a radiation-sensitive composition. The resist film is exposed. The exposed resist film is developed using a developer solution. The developer solution includes no less than 80% by mass of an organic solvent. The radiation-sensitive composition includes at least two components including a first polymer and a radiation-sensitive acid generator. The first polymer includes a structural unit having an acid-labile group. One or more components of the radiation-sensitive composition have a group represented by a formula (1).

-A$^-$X$^+$     (1)

In the formula (1), A$^-$ represents —N$^-$—SO$_2$—R$^D$, —COO$^-$, —O$^-$ or —SO$_3^-$. In a case where A$^-$ represents —SO$_3^-$, —SO$_3^-$ does not directly bond to a carbon atom having a fluorine atom. R$^D$ represents a linear or branched monovalent hydrocarbon group having 1 to 10 carbon atoms or a cyclic monovalent hydrocarbon group having 3 to 20 carbon atoms. A part or all of hydrogen atoms of the hydrocarbon group represented by R$^D$ are not substituted or substituted by a fluorine atom. X$^+$ represents an onium cation.

According to another aspect of the present invention, a radiation-sensitive composition includes at least two components including a first polymer and a radiation-sensitive acid generator. The first polymer includes a structural unit having an acid-labile group. One or more components of the radiation-sensitive composition have a group represented by a formula (1). The radiation-sensitive resin composition is for use in a resist pattern-forming method. The resist pattern-forming method includes providing a resist film on a substrate using the radiation-sensitive composition. The resist film is exposed. The exposed resist film is developed.

-A$^-$X$^+$     (1)

In the formula (1), A$^-$ represents —N$^-$—SO$_2$—R$^D$, —COO$^-$, —O$^-$ or —SO$_3^-$. In a case where A$^-$ represents —SO$_3^-$, —SO$_3^-$ does not directly bond to a carbon atom having a fluorine atom. R$^D$ represents a linear or branched monovalent hydrocarbon group s having 1 to 10 carbon atoms or a cyclic monovalent hydrocarbon group having 3 to 20 carbon atoms. A part or all of hydrogen atoms of the hydrocarbon group represented by R$^D$ are not substituted or substituted by a fluorine atom. X$^+$ represents an onium cation.

DESCRIPTION OF THE EMBODIMENTS

A pattern-forming method according to an embodiment of the present invention made for solving the foregoing problems includes the steps of:

(1) providing a resist film on a substrate using a radiation-sensitive composition;

(2) exposing the resist film; and (3) developing the exposed resist film, in which a developer solution in the development step (3) contains no less than 80% by mass of an organic solvent, and the radiation-sensitive composition contains at least two components including:

(A) a polymer that includes a structural unit having an acid-labile group (hereinafter, may be also referred to as "polymer (A)"); and (B) a radiation-sensitive acid generator (hereinafter, may be also referred to as "acid generator (B)"), one or more components of the radiation-sensitive composition having a group represented by the following formula (1):

-A$^-$X$^+$     (1)

wherein, in the formula (1),

A$^-$ represents —N$^-$—SO$_2$—R$^D$, —COO$^-$, —O$^-$ or —SO$_3^-$, wherein in a case where A$^-$ represents —SO$_3^-$, —SO$_3^-$ does not directly bond to a carbon atom having a fluorine atom; R$^D$ represents a linear or branched monovalent hydrocarbon group having 1 to 10 carbon atoms or a cyclic monovalent hydrocarbon group having 3 to 20 carbon atoms, wherein a part or all of hydrogen atoms of the hydrocarbon group represented by R$^D$ are not substituted or substituted by a fluorine atom; and X$^+$ represents an onium cation.

The pattern-forming method of the embodiment of the present invention is first characterized in that as a developer solution for use in the development step, a developer solution having a hydrophobicity higher than that of aqueous alkali solutions commonly used in formation of a positive type chemically amplified resist, i.e., a developer solution containing no less than 80% by mass of an organic solvent (a developer solution capable of dissolving light-unexposed sites of a resist film to form a negative pattern) is used. Such an organic solvent is superior in an affinity for the surface of a resist film, and can consequently improve resolution.

In addition, the radiation-sensitive composition of the embodiment of the present invention for use in the pattern-forming method is further characterized in that: the composition contains at least two components including the polymer (A) and the acid generator (B); and one or more components of the radiation-sensitive composition has the group represented by the above formula (1). In the exposure step, the acid-labile group included in the polymer (A) is dissociated by an action of an acid generated from the acid generator (B). As a result, hydrophilicity of the polymer (A) at light-exposed sites increases, leading to a poorer solubility in a developer solution having a comparatively high hydrophobicity used in the embodiment of the present invention, whereas dissolution in the developer solution of the polymer in the resist film at light-unexposed sites is accelerated. Furthermore, the one or more components having the group represented by the above formula (1) generates an acid at light-exposed sites to enhance an insolubility of the polymer (A) in a developer solution, and as a result, roughness of the surface at light-exposed sites after development is prevented. On the other hand, a more superior acid-capturing function by an anion is exhibited at light-unexposed sites, thereby serving as a quencher, and thus an acid diffused from the light-exposed sites is captured. In other words, the function as a quencher is exhibited only at light-unexposed sites; therefore, a contrast of a deprotecting reaction is improved, and as a result further improvement of a resolution is enabled.

To the contrary, in conventional radiation-sensitive compositions containing a quencher component, the component serves as a quencher irrespective of whether the sites are light-exposed or light-unexposed; therefore, the effect of improving the as described above is not necessarily sufficiently achieved, and as a result, the resolution may be also unsatisfactory. Furthermore, an affinity for a developer solution increases at light-exposed sites, and as a result, roughness may occur.

On the other hand, the missing contact holes are more likely to be generated as a transpiration rate of the quencher component is greater, due to promotion of a deprotecting reaction in the upper layer portion of the resist film. However, transpiration of the one or more components having the group represented by the above formula (1) included in the composition is less likely to occur, and homogeneous distribution in the resist film is enabled. As a result, generation of missing contact holes can be suppressed.

Therefore, a combination of the composition with the pattern-forming method enables generation of roughness of the surface of light-exposed sites and missing contact hole after development to be suppressed, and also enables a pattern that is superior in lithography characteristics such as circularity to be formed.

In the pattern-forming method, the radiation-sensitive composition preferably contains, as the component having a group represented by the above formula (1), (C) a compound represented by the formula (2) (hereinafter, may be also referred to as "compound (C)").

In the formula (2), $R^1$ represents a hydrogen atom or a monovalent organic group; and $A^-$ and $X^+$ are as defined in the above formula (1).

The composition may include the one or more components having the group represented by the above formula (1) in a form of the compound (C), according to one manner of inclusion of the one or more components. Such an inclusion mode is advantageous in that the composition can be comparatively readily prepared.

In the pattern-forming method, it is preferred that the polymer (A) further includes a structural unit derived from a compound represented by the following formula (3-1), a compound represented by the following formula (3-2) or a combination thereof. In addition, in the pattern-forming method, the composition may further contain (D) a polymer (hereinafter, may be also referred to as "polymer (D)") that includes a structural unit derived from the compound represented by the following formula (3-1), the compound represented by the following formula (3-2) or a combination thereof.

In the formula (3-1), $A^-$ and $X^+$ are as defined in the above formula (1);

$R^2$ represents a hydrogen atom, a methyl group or a trifluoromethyl group;

$R^3$ and $R^5$ each independently represent a single bond, a linear or branched divalent hydrocarbon group having 1 to 10 carbon atoms, or a divalent hydrocarbon group that includes a cyclic structure and has 3 to 20 carbon atoms, wherein a part or all of hydrogen atoms of these hydrocarbon groups are not substituted or substituted by a fluorine atom, and wherein in a case where $A^-$ represents $-SO_3^-$, $-SO_3^-$ does not directly bond to a carbon atom having a fluorine atom; and $R^4$ represents a single bond, $-O-$, $-C(=O)-$, $-C(=O)-O-$, $-O-C(=O)-$ or a sulfinyl group.

In the formula (3-2), $A^-$ and $X^+$ are as defined in the above formula (1); and $R^{2'}$ represents a hydrogen atom, a methyl group or a trifluoromethyl group.

With respect to the manner of inclusion of the one or more components having the group represented by the above formula (1) in the composition, the polymer (A) may be included in a form further including a structural unit derived from at least one selected from the group consisting of the compound represented by the above formula (3-1) and the compound represented by the above formula (3-2). Also, a manner in which the composition further contains the polymer (D) is acceptable. Since the group represented by the above formula (1) is uniformly distributed in a resist film according to these forms of inclusion, effects of the embodiment of the present invention are even further improved.

$X^+$ is preferably represented by the following formula (4):

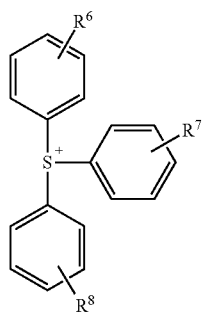

(4)

wherein, in the formula (4), $R^6$ to $R^8$ each independently represent a hydrogen atom, a halogen atom, a hydroxyl group, an alkyl group having 1 to 10 carbon atoms, a cycloalkyl group having 3 to 12 carbon atoms, or an alkoxy group having 1 to 10 carbon atoms, each not having or having a substituent.

When a sulfonium cation having the specific structure represented by the above formula (4) is used as the cation represented by $X^+$, dispersibility of the polymer (A) in a resist coating film is enhanced, and thus effects of the embodiment of the present invention are particularly improved.

The radiation-sensitive composition of the embodiment of the present invention contains at least two components including:

(A) a polymer that includes a structural unit having an acid-labile group; and (B) a radiation-sensitive acid generator, one or more components of the radiation-sensitive composition having a group represented by the following formula (1), the radiation-sensitive resin composition being for use in a resist pattern-forming method including the steps of:

(1) providing a resist film on a substrate using the radiation-sensitive composition;

(2) exposing the resist film; and (3) developing the exposed resist film.

In the formula (1), $A^-$ represents $-N^-$—$SO_2$—$R^D$, $-COO^-$, $-O^-$ or $-SO_3^-$, wherein in a case where $A^-$ represents $-SO_3^-$, $-SO_3^-$ does not directly bond to a carbon atom having a fluorine atom;

$R^D$ represents a linear or branched monovalent hydrocarbon group having 1 to 10 carbon atoms or a cyclic monovalent hydrocarbon group having 3 to 20 carbon atoms, wherein a part or all of hydrogen atoms of the hydrocarbon group represented by $R^D$ are not substituted or substituted by a fluorine atom; and $X^+$ represents an onium cation.

By using the radiation-sensitive composition in the pattern-forming method described above, generation of roughness of the surface of light-exposed sites and missing contact hole after development can be suppressed, and a pattern that is superior in lithography characteristics such as resolution and circularity can be obtained.

According to the embodiments of the present invention, a pattern-forming method that suppresses generation of roughness of the surface of light-exposed sites and missing contact hole after development, and that is superior in lithography characteristics such as resolution and circularity can be provided. Also, a radiation-sensitive composition suited for the pattern-forming method can be provided. Therefore, the embodiment of the present invention is suited for microfabrication by way of lithography. The embodiments will now be described in detail.

Pattern-Forming Method

The pattern-forming method of the embodiment of the present invention includes the steps of: (1) providing a resist film on a substrate using a radiation-sensitive composition (hereinafter, may be also referred to as "step (1)"); (2) exposing the resist film (hereinafter, may be also referred to as "step (2)"); and (3) developing the exposed resist film (hereinafter, may be also referred to as "step (3)"), in which a developer solution in the step (3) contains no less than 80% by mass of an organic solvent, and the radiation-sensitive composition contains at least two components including: (A) a polymer; and (B) an acid generator, in which one or more components of the radiation-sensitive composition has a group represented by the above formula (1). A combination of the composition with the pattern-forming method enables generation of roughness of the surface of light-exposed sites and missing contact hole after development to be suppressed, and a pattern that is superior in lithography characteristics such as circularity to be formed. Hereinafter, each step will be described in detail.

Step (1)

In this step, the radiation-sensitive composition of the embodiment of the present invention is coated on a substrate to provide a resist film. As the substrate, for example, conventionally well-known substrates such as a silicon wafer and a wafer coated with aluminum can be used. In addition, organic or inorganic antireflective films disclosed in, for example, Japanese Examined Patent Application, Publication No. H06-12452, Japanese Unexamined Patent Application, Publication No. S59-93448, and the like may be provided on the substrate.

A coating method is exemplified by spin-coating, cast coating, roll coating, and the like. It is to be noted that the film thickness of the resist film provided is typically 0.01 μm to 1 μm, and preferably 0.01 μm to 0.5 μm.

After coating the composition, a solvent in the coating film may be volatilized as needed by prebaking (PB). According to heating conditions of PB, the temperature may be appropriately selected depending on the formulation of the photoresist composition, and is typically about 30° C. to 200° C. and preferably 50° C. to 150° C. The heating time period is appropriately selected in accordance with the blend formulation of the composition.

A protective film as disclosed in Japanese Unexamined Patent Application, Publication No. H05-188598 or the like may be provided on the resist layer so as to prevent influences from basic impurities and the like contained in the environmental atmosphere. Furthermore, in order to prevent outflow of the acid generating agent and the like from the resist layer, a liquid immersion lithography protective film as disclosed in Japanese Unexamined Patent Application, Publication No. 2005-352384 or the like may be provided on the resist layer. These techniques may be used in combination.

Step (2)

In this step, the resist film provided in the step (1) is exposed at a desired region by carrying out reduction projection through a mask having a specific pattern, and an immersion liquid as needed. For example, an isolated trench (iso-trench) pattern can be formed by carrying out reduced projection exposure at a desired region through a mask having an isolated line (iso-line) pattern. Also, the exposure may be carried out at least twice depending on the desired pattern and the mask pattern. When the exposure is carried out at least twice, the exposure is preferably carried out continuously. When the exposure is carried out a plurality of times, for example, first reduced projection exposure is carried out through a line-and-space pattern mask at a desired region, and subsequently second reduced projection exposure is carried out such that lines cross over light-exposed sites subjected to the first exposure. The first light-exposed sites are preferably orthogonal to the second light-exposed sites. Due to being orthogonal with each other, a contact hole pattern of substantially perfect circles can be easily formed at light-unexposed sites surrounded by light-exposed sites. It is to be noted that examples of the immersion liquid for use in the exposure include water, a fluorine-containing inert liquid, and the like. It is preferred that the immersion liquid be transparent to the exposure wavelength, and has a temperature coefficient of the refractive index as small as possible so that distortion of an optical image projected onto the film is minimized. When using an ArF excimer laser (wavelength: 193 nm) as the exposure light source, it is preferred to use water from the viewpoint of availability and ease of handling, in addition to the viewpoints described above. When water is used, a slight amount of an additive which reduces the surface tension of water and imparts enhanced surface activity may be added. It is preferred that the additive hardly dissolves a resist layer on a wafer and has a negligible influence on an optical coating of an inferior face of a lens. The water for use is preferably distilled water.

A radioactive ray used for the exposure is appropriately selected in accordance with the type of the acid generator (B), and is exemplified by an ultraviolet ray, a far ultraviolet ray, an X-ray, a charged particle ray, and the like. Among these, a far ultraviolet ray typified by an ArF excimer laser or a KrF excimer laser (wavelength: 248 nm) is preferred, and an ArF excimer laser is more preferred. The exposure conditions such as an exposure dose are appropriately selected in accordance with the formulation, and type of additives etc. of the composition. The pattern-forming method of the embodiment of the present invention may include a plurality of the exposure steps, and light sources employed in the exposure carried out a plurality of times may be identical or different, but an ArF excimer laser beam is preferably used in the first exposure.

In addition, it is preferred that post-exposure baking (PEB) is carried out after the exposure. When the PEB is carried out, a dissociation reaction of an acid-labile group in the composition can smoothly proceed. According to heating conditions of PEB, the temperature may be typically 30° C. to 200° C., and preferably 50° C. to 170° C.

Step (3)

In this step, after the exposure in the step (2), development is carried out using a negative developer solution containing no less than 80% by mass of an organic solvent to form a pattern. The negative developer solution as referred to means a developer solution that selectively dissolve and remove poorly light-exposed sites and light-unexposed sites. The organic solvent contained in the negative developer solution is preferably an alcohol solvent, an ether solvent, a ketone organic solvent, an amide solvent, an ester organic solvent, a hydrocarbon solvent or a combination thereof.

Examples of the alcohol solvent include:

monohydric alcohol solvents such as methanol, ethanol, n-propanol, iso-propanol, n-butanol, iso-butanol, sec-butanol, tert-butanol, n-pentanol, iso-pentanol, 2-methylbutanol, sec-pentanol, tert-pentanol, 3-methoxybutanol, n-hexanol, 2-methylpentanol, sec-hexanol, 2-ethylbutanol, sec-heptanol, 3-heptanol, n-octanol, 2-ethylhexanol, sec-octanol, n-nonyl alcohol, 2,6-dimethyl-4-heptanol, n-decanol, sec-undecyl alcohol, trimethylnonyl alcohol, sec-tetradecyl alcohol, sec-heptadecyl alcohol, furfuryl alcohol, phenol, cyclohexanol, methylcyclohexanol, 3,3,5-trimethylcyclohexanol, benzyl alcohol and diacetone alcohol;

polyhydric alcohol solvents such as ethylene glycol, 1,2-propylene glycol, 1,3-butylene glycol, 2,4-pentanediol, 2-methyl-2,4-pentanediol, 2,5-hexanediol, 2,4-heptanediol, 2-ethyl-1,3-hexanediol, diethylene glycol, dipropylene glycol, triethylene glycol and tripropylene glycol;

partially etherified polyhydric alcohol solvents such as ethylene glycol monomethyl ether, ethylene glycol monoethyl ether, ethylene glycol monopropyl ether, ethylene glycol monobutyl ether, ethylene glycol monohexyl ether, ethylene glycol monophenyl ether, ethylene glycol mono-2-ethylbutyl ether, diethylene glycol monomethyl ether, diethylene glycol monoethyl ether, diethylene glycol monopropyl ether, diethylene glycol monobutyl ether, diethylene glycol monohexyl ether, propylene glycol monomethyl ether, propylene glycol monoethyl ether, propylene glycol monopropyl ether, propylene glycol monobutyl ether, dipropylene glycol monomethyl ether, dipropylene glycol monoethyl ether and dipropylene glycol monopropyl ether, and the like.

Examples of the ether solvent include diethyl ether, dipropyl ether, dibutyl ether, diphenyl ether, methoxybenzene, and the like.

Examples of the ketone solvent include acetone, methyl ethyl ketone, methyl n-propyl ketone, methyl n-butyl ketone, diethyl ketone, methyl isobutyl ketone, methyl n-pentyl ketone, ethyl n-butyl ketone, methyl n-hexyl ketone, di-isobutyl ketone, trimethylnonanone, cyclopentanone, cyclohexanone, cycloheptanone, cyclooctanone, methylcyclohexanone, 2,4-pentanedione, acetonyl acetone, acetophenone, and the like.

Examples of the amide solvent include N,N'-dimethylimidazolidinone, N-methylformamide, N,N-dimethylformamide, N,N-diethylformamide, acetamide, N-methylacetamide, N,N-dimethylacetamide, N-methylpropionamide, N-methylpyrrolidone, and the like.

Examples of the ester solvent include diethyl carbonate, propylene carbonate, methyl acetate, ethyl acetate, γ-butyrolactone, γ-valerolactone, n-propyl acetate, isopropyl acetate, n-butyl acetate, isobutyl acetate, sec-butyl acetate, n-pentyl acetate, sec-pentyl acetate, 3-methoxybutyl acetate, methylpentyl acetate, 2-ethylbutyl acetate, 2-ethylhexyl acetate, benzyl acetate, cyclohexyl acetate, methylcyclohexyl acetate, n-nonyl acetate, methyl acetoacetate, ethyl acetoacetate, ethylene glycol monomethyl ether acetate, ethylene glycol monoethyl ether acetate, diethylene glycol monomethyl ether acetate, diethylene glycol monoethyl ether acetate, diethylene glycol mono-n-butyl ether acetate, propylene glycol monomethyl ether acetate, propylene glycol monoethyl ether acetate, propylene glycol monopropyl ether acetate, propylene glycol monobutyl ether acetate, dipropylene glycol monomethyl ether acetate, dipropylene glycol monoethyl ether acetate, diglycol acetate, methoxytriglycol acetate, iso-amyl acetate, ethyl propionate, n-butyl propionate, iso-amyl propionate, diethyl oxalate, di-n-butyl oxalate, methyl lactate, ethyl lactate, n-butyl lactate, n-amyl lactate, diethyl malonate, dimethyl phthalate, diethyl phthalate, and the like.

Examples of the hydrocarbon solvent include:

aliphatic hydrocarbon solvents such as n-pentane, iso-pentane, n-hexane, iso-hexane, n-heptane, iso-heptane, 2,2,4-trimethylpentane, n-octane, iso-octane, cyclohexane, and methylcyclohexane;

aromatic hydrocarbon solvents such as benzene, toluene, xylene, mesitylene, ethylbenzene, trimethylbenzene, methylethylbenzene, n-propylbenzene, isopropylbenzene, diethylbenzene, isobutylbenzene, triethylbenzene, di-isopropylbenzene, n-amylnaphthalene, and the like.

Of these, n-butyl acetate, isopropyl acetate, iso-amyl acetate, methyl ethyl ketone, methyl n-butyl ketone, methyl n-pentyl ketone and methyl n-amyl ketone are preferred. These organic solvents may be used either alone, or in combination of two or more thereof.

The content of the organic solvent in the developer solution is no less than 80% by mass. When the content of the organic solvent in the developer solution is no less than 80% by mass, a contrast of the pattern resulting from exposure can be improved, and as a result, formation of a pattern that is superior in development characteristics and lithography characteristics is enabled. It is to be noted that examples of a component other than the organic solvent include water, silicone oil, and the like.

A surfactant may be added to the developer solution in an appropriate amount as needed. As the surfactant, for example, an ionic or nonionic fluorochemical surfactant and/or a silicone surfactant, and the like may be used.

Examples of the development method include a dipping method that immerses the substrate in a container filled with the developer for a given time, a puddle method that allows the developer to be present on the surface of the substrate due to surface tension for a given time, a spraying method that sprays the developer onto the surface of the substrate, a dynamic dispensing method that applies the developer to the substrate that is rotated at a constant speed while scanning with a developer application nozzle at a constant speed, and the like.

In the pattern-forming method, the resist film is preferably rinsed with a rinse agent after the development in the step (3). As the rinse agent, an organic solvent may be preferably used similarly to the developer solution, whereby scum generated can be efficiently washed away. The rinse agent is preferably a hydrocarbon solvent, a ketone solvent, an ester solvent, an alcohol solvent, an amide solvent, or the like. Of these, an alcohol solvent and an ester solvent are preferred, and a monovalent alcohol solvent having 6 to 8 carbon atoms is more preferred. The monovalent alcohol having 6 to 8 carbon atoms is exemplified linear, branched or cyclic monovalent alcohols, and examples thereof include 1-hexanol, 1-heptanol, 1-octanol, 4-methyl-2-pentanol, 2-hexanol, 2-heptanol, 2-octanol, 3-hexanol, 3-heptanol, 3-octanol, 4-octanol, benzyl alcohol, and the like. Of these, 1-hexanol, 2-hexanol, 2-heptanol, and 4-methyl-2-pentanol are preferred.

Each component of the rinse agent may be used either alone, or in combination of two or more thereof. The moisture content of the rinse agent is preferably no greater than 10% by mass, more preferably no greater than 5% by mass, and particularly preferably no greater than 3% by mass. When the moisture content is no greater than 10% by mass, favorable development characteristics can be attained. It is to be noted that, a surfactant described later may be added to the rinse agent.

Examples of the rinsing method include a spinning method that applies the rinse agent to the substrate that is rotated at a constant speed, a dipping method that immerses the substrate in a container filled with the rinse agent for a given time, a spraying method that sprays the rinse agent onto the surface of the substrate, and the like.

Radiation-Sensitive Composition

The radiation-sensitive composition for use in the embodiment of the present invention contains at least two components including the polymer (A) and the acid generator (B), in which one or more components of the radiation-sensitive composition has a group represented by the above formula (1). In addition, the composition may contain optional component(s) as long as the effects of the present invention are not impaired. Hereinafter, each component will be described in detail.

(A) Polymer

The polymer (A) includes a structural unit having an acid-labile group (hereinafter, may be also referred to as "structural unit (I)"), and is provided as a base resin in the radiation-sensitive composition. In addition, the polymer (A) may also have other structural unit such as a structural unit that includes a lactone structure, etc., (hereinafter, may be also referred to as "structural unit (II)"). Hereinafter, each structural unit will be described in detail.

Structural Unit (I)

The structural unit (I) is preferably a structural unit represented by the following formula.

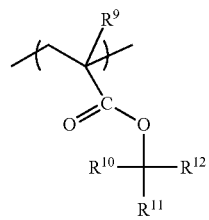

In the above formula, $R^9$ represents a hydrogen atom, a fluorine atom, a methyl group or a trifluoromethyl group; $R^{10}$ to $R^{12}$ each independently represent a linear or branched alkyl group having 1 to 10 carbon atoms, wherein $R^{10}$ and $R^{11}$ may taken together represent a divalent alicyclic hydrocarbon group having 3 to 20 carbon atoms together with the carbon atom to which $R^{10}$ and $R^{11}$ bond.

Examples of the linear or branched alkyl group having 1 to 10 carbon atoms represented by $R^{10}$ to $R^{12}$ include a methyl group, an ethyl group, a n-propyl group, an i-propyl group, a 1-butyl group, an i-butyl group, a sec-butyl group, a tert-butyl group, a n-pentyl group, an i-pentyl group, a sec-pentyl group, a neo-pentyl group, a tert-pentyl group, a n-hexyl group, an i-hexyl group, a n-heptyl group, an i-heptyl group, a n-octyl group, an i-octyl group, a n-nonyl group, an i-nonyl group, a n-decyl group, an i-decyl group, and the like.

Examples of the divalent alicyclic hydrocarbon group having 3 to 20 carbon atoms which may be taken together represented by $R^{10}$ and $R^{11}$ together with the carbon atom to which $R^{10}$ and $R^{11}$ bond include groups derived by removing two hydrogen atoms from an alicyclic hydrocarbon such as cyclopropane, cyclobutane, cyclopentane, cyclohexane, dicyclopentane, norbornane, tricyclodecane, tetracyclododecane or adamantane.

$R^{10}$ to $R^{12}$ represent preferably a linear or branched alkyl group having 1 to 8 carbon atoms, and more preferably a linear or branched alkyl group having 1 to 6 carbon atoms.

Specific examples of the structural unit (I) include structural units represented by the following formulae.

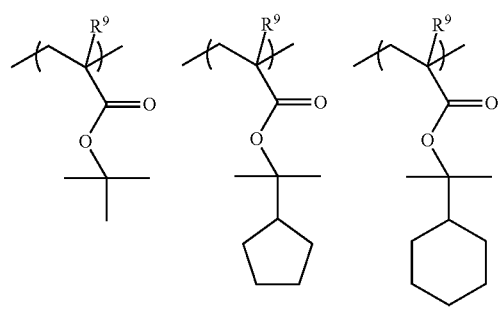

-continued

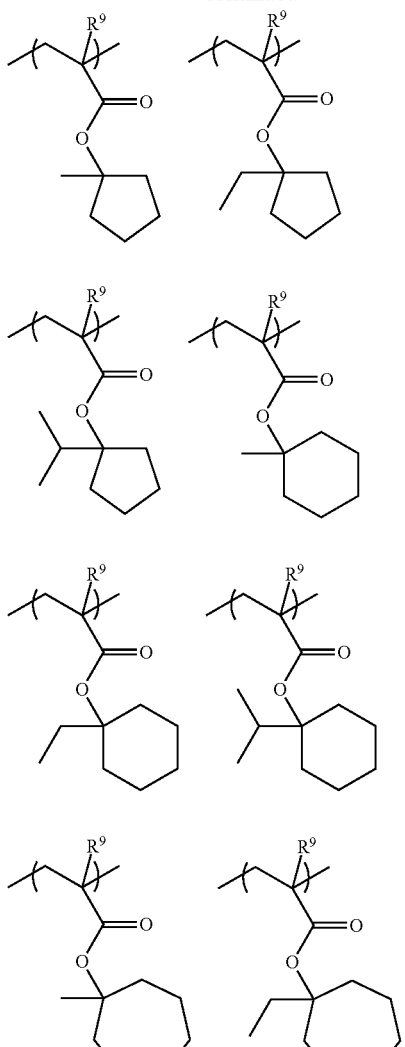

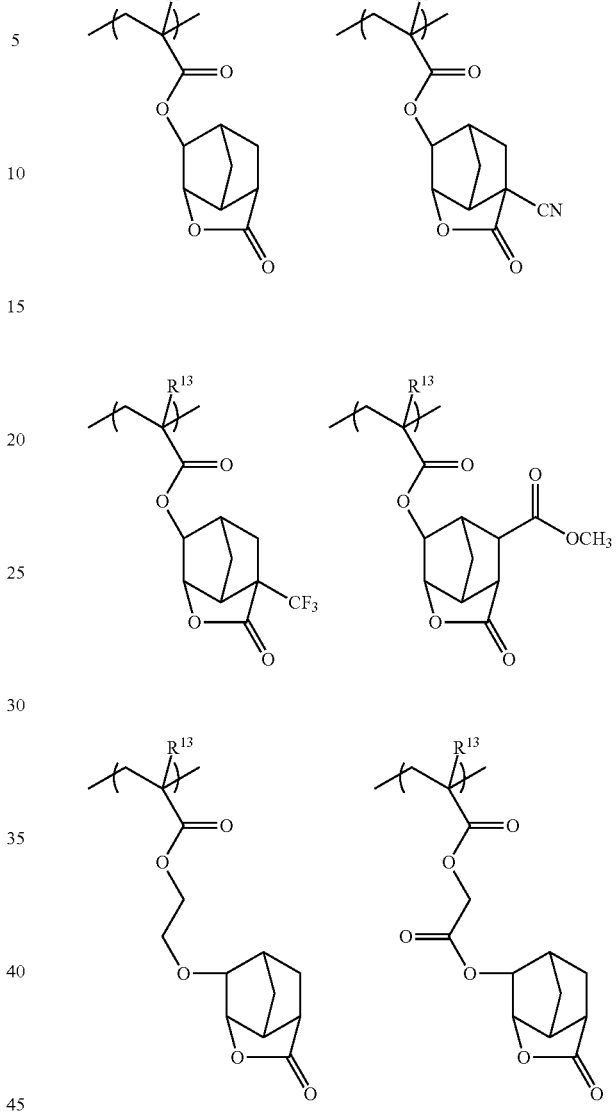

In the above formulae, $R^9$ represents a hydrogen atom, a fluorine atom, a methyl group or a trifluoromethyl group.

The proportion of the structural unit (I) contained in the polymer (A) is preferably no less than 10 mol %, more preferably 20 to 80 mol %, and particularly preferably 30 to 70 mol % with respect to the entire structural units constituting the polymer (A). When the proportion of the structural unit (I) falls within the above range, lithography performances of the resultant resist pattern are further improved. The polymer (A) may include either one type alone, or two or more types of the structural unit (I).

Structural Unit (II)

The polymer (A) may further include a structural unit having at least one structure selected from the group consisting of a lactone structure and a cyclic carbonate structure as the structural unit (II). When the polymer (A) has the structural unit (II), adhesiveness of a resist coating film obtained from the radiation-sensitive composition is improved.

The structural unit (II) is exemplified by structural units represented by the following formulae, and the like.

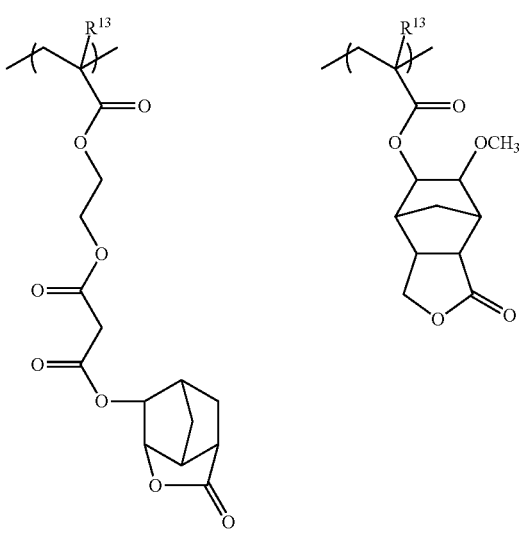

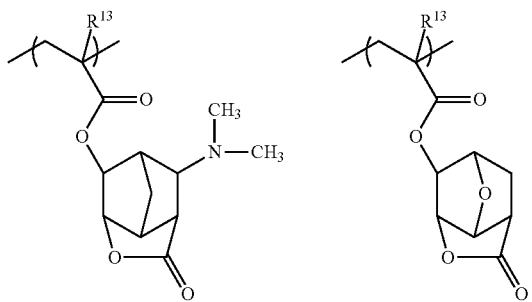

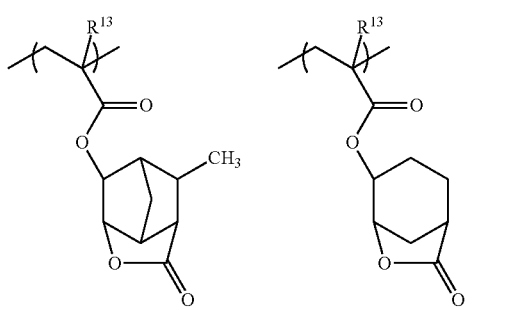

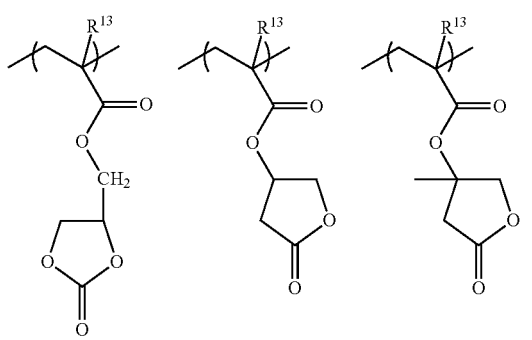

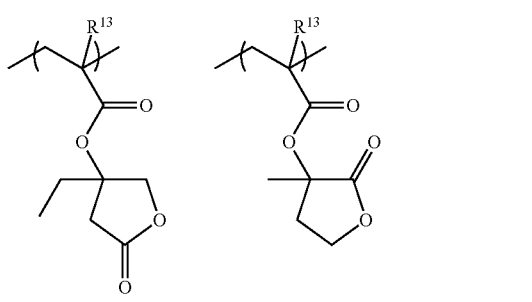

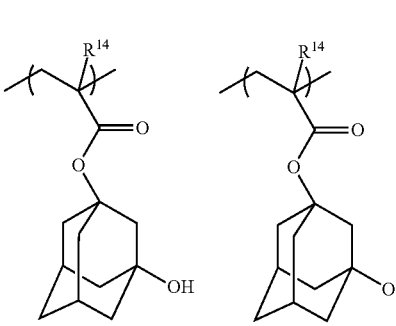

In the above formulae, $R^{13}$ represents a hydrogen atom, a fluorine atom, a methyl group or a trifluoromethyl group.

The proportion of the structural unit (II) contained in the polymer (A) is preferably 0 to 70 mol %, and more preferably 20 to 65 mol % with respect to the entire structural units constituting the polymer (A). When the proportion of the structural unit (II) falls within the above range, adhesiveness of the resultant resist pattern is improved, and resistance to pattern collapse, and the like can be improved. The polymer (A) may include either one type alone, or two or more types of the structural unit (II).

Structural Unit (III)

The polymer (A) may further include structural unit having a hydrophilic functional group(hereinafter, may be also referred to as "structural unit (III)"). When the polymer (A) has the structural unit (III), lithography performances of the resist pattern can be further improved.

The structural unit (III) is exemplified by structural units represented by the following formulae.

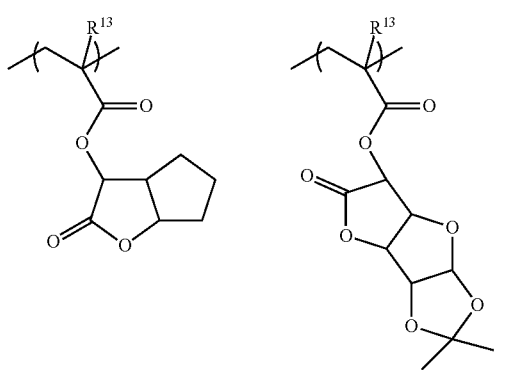

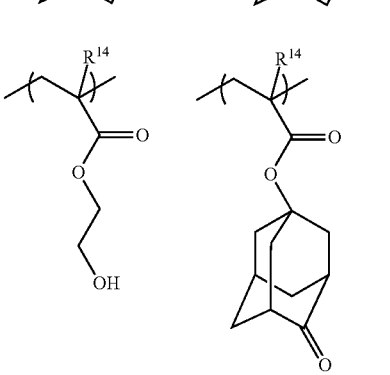

-continued

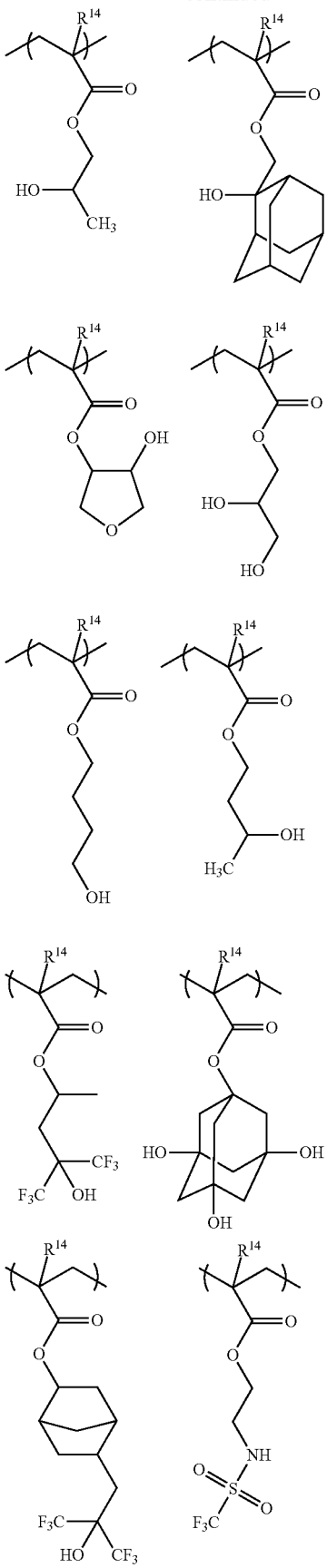

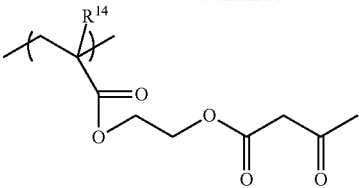

In the above formula, $R^{14}$ represents a hydrogen atom, a fluorine atom, a methyl group or a trifluoromethyl group.

The proportion of the structural unit (III) contained in the polymer (A) is preferably 0 to 30 mol %, and more preferably 0 to 20 mol % with respect to the entire structural units constituting the polymer (A). The polymer (A) may include either one type alone, or two or more types of the structural unit (III).

It is preferred that the polymer (A) further includes a structural unit derived from a compound represented by the formula (3-1), a compound represented by the formula (3-2) or a combination thereof (hereinafter, may be also referred to as "structural unit (IV)"). The structural unit (IV) will be described later. Moreover, the polymer (A) may include structural unit(s) in addition to the structural units (I) to (IV) within a range not leading to impairment of the effects of the present invention.

In the radiation-sensitive composition, the content of the polymer (A) with respect to the total amount of the solid content, i.e., entire components other than the solvent, is preferably no less than 50% by mass, more preferably no less than 60% by mass, and still more preferably no less than 70% by mass. The radiation-sensitive composition may include either one type alone, or two or more types of the polymer (A).

Synthesis Method of Polymer (A)

The polymer (A) may be prepared, for example, by polymerizing the monomer corresponding to each predetermined structural unit in an appropriate solvent using a radical polymerization initiator. For example, it is preferred to synthesize the polymer (A) by: a method in which a solution containing a monomer and a radical initiator is added dropwise to another solution containing a reaction solvent or the monomer, and the mixture is polymerized; a method in which a solution containing a monomer and a solution containing a radical initiator are each separately added dropwise to another solution containing a reaction solvent or the monomer, and the mixture is polymerized; a method in which a plurality of solutions each containing a single monomer and a solution containing a radical initiator are each separately added dropwise to another solution containing a reaction solvent or the monomer, and the mixture is polymerized; and the like.

The reaction temperature in the method described above may be appropriately determined in accordance of the type of the initiator. The reaction temperature is typically 30° C. to 180° C., preferably 40° C. to 160° C., and still more preferably 50° C. to 140° C. The time period of the dropwise addition may vary depending on conditions such as reaction temperature, initiator type, the monomer to be reacted and the like, and is typically, 30 min to 8 hrs, preferably 45 min to 6 hrs, and more preferably 1 hr to 5 hrs. In addition, the total reaction time including the dropwise addition may also vary similarly to the time period of the dropwise addition, and is typically 30 min to 8 hrs, preferably 45 min to 7 hrs, and more preferably 1 hr to 6 hrs.

The radical initiator for use in the polymerization is exemplified by azobisisobutyronitrile (AIBN), 2,2'-azobis(4- methoxy-2,4-dimethylvaleronitrile), 2,2'-azobis(2-cyclopropylpropionitrile), 2,2'-azobis(2,4-dimethylvaleronitrile), dimethyl 2,2'-azobisisobutyrate, and the like. These initiators may be used either alone or as a mixture of two or more thereof.

A solvent for polymerization is not limited as long as the solvent is other than those that inhibit polymerization (nitrobenzene having a polymerization inhibitory effect, mercapto compounds having a chain transfer effect, etc.), and is capable of dissolving the monomer. Examples of the solvent for polymerization include alcohol solvents, ketone solvents, amide solvents, ester lactone solvents, nitrile solvents and mixed solvents thereof, and the like. These solvents may be used either alone or in combination of two or more types thereof.

The resin obtained by the polymerization reaction may be collected preferably by a reprecipitation technique. More specifically, after the polymerization reaction is completed, the polymerization mixture is charged into a solvent for reprecipitation, whereby a target resin is collected in a powdery form. As the reprecipitation solvent, an alcohol, an alkane or the like may be used either alone or as a mixture of two or more thereof. Alternatively to the reprecipitation technique, liquid separating operation, column operation, ultrafiltration operation or the like may be employed to collect the resin through eliminating low molecular components such as monomers and oligomers.

Although the weight average molecular weight (Mw) in terms of the polystyrene equivalent of the polymer (A) as determined by a gel permeation chromatography (GPC) method is not particularly limited, the Mw is preferably no less than 1,000 and no greater than 50,000, more preferably no less than 2,000 and no greater than 40,000, and particularly preferably no less than 3,000 and no greater than 30,000. It is to be noted that when the Mw of the polymer (A) is less than 1,000, heat resistance when provided as a resist tends to be inferior. On the other hand, the Mw of the polymer (A) exceeding 50,000 is likely to result in deteriorated developability of the resultant resist.

Also, a ratio (Mw/Mn) of the Mw of the polymer (A) to a number average molecular weight in terms of the polystyrene equivalent (Mn) as determined by GPC is typically 1 or greater and 5 or less, preferably no less than 1 and no greater than 3, and more preferably no less than 1 and no greater than 2. When the Mw/Mn falls within this range, the photoresist film may have a superior resolving performance.

The Mw and the Mn as referred to herein are values determined by GPC using GPC columns (Tosoh Corporation, G2000HXL×2, G3000HXL×1, G4000HXL×1) under analytic conditions involving a flow rate of 1.0 ml/min, an elution solvent of tetrahydrofuran and a column temperature of 40° C., with mono-dispersed polystyrene as a standard.

(B) Acid Generator

The acid generator (B) generates an acid upon exposure, and the acid allows an acid-labile group present in the polymer (A) to be dissociated, thereby generating an acid. The mode of incorporation of the acid generator (B) into the composition may be any of a form of being incorporated as a compound as described below (hereinafter, may be appropriately referred to as "acid generating agent (B)"), a form of being incorporated as a part of a polymer, or a combination of these two forms. It is to be noted that an ArF excimer laser beam is suitably used as an exposure light in the embodiment of the present invention, and thus the polymer contained in the radiation-sensitive composition preferably has a structure that absorbs less ArF excimer laser beam. Since the polymer (A), etc., can be used as such a polymer, the acid generator (B) is required to generate an acid that is sufficiently strong for allowing the acid-labile group included in the polymer (A) to be dissociated.

The acid generating agent (B) is exemplified by an onium salt compound, a sulfonimide compound, a halogen-containing compound, a diazo ketone compound, and the like. Of these acid generating agents (B), an onium salt compound is preferred.

The onium salt compound is exemplified by a sulfonium salt, a tetrahydrothiophenium salt, an iodonium salt, a phosphonium salt, a diazonium salt, a pyridinium salt, and the like.

Examples of the sulfonium salt include triphenylsulfonium trifluoromethanesulfonate, triphenylsulfonium nonafluoro-n-butanesulfonate, triphenylsulfonium perfluoro-n-octanesulfonate, triphenylsulfonium 2-bicyclo[2.2.1]hept-2-yl-1,1,2,2-tetrafluoroethanesulfonate, 4-cyclohexylphenyldiphenylsulfonium trifluoromethanesulfonate, 4-cyclohexylphenyldiphenylsulfonium nonafluoro-n-butanesulfonate, 4-cyclohexylphenyldiphenylsulfonium perfluoro-n-octanesulfonate, 4-cyclohexylphenyldiphenylsulfonium 2-bicyclo[2.2.1]hept-2-yl-1,1,2,2-tetrafluoroethanesulfonate, 4-methanesulfonylphenyldiphenylsulfonium trifluoromethanesulfonate, 4-methanesulfonylphenyldiphenylsulfonium nonafluoro-n-butanesulfonate, 4-methanesulfonylphenyldiphenylsulfonium perfluoro-n-octanesulfonate, 4-methanesulfonylphenyldiphenylsulfonium 2-bicyclo[2.2.1]hept-2-yl-1,1,2,2-tetrafluoroethanesulfonate, triphenylsulfonium 1,1,2,2-tetrafluoro-6-(1-adamantanecarbonyloxy)-hexane-1-sulfonate, and the like. Among these, triphenylsulfonium trifluoromethanesulfonate, triphenylsulfonium nonafluoro-n-butanesulfonate, and triphenylsulfonium-1,1,2,2-tetrafluoro-6-(1-adamantanecarbonyloxy)-hexane-1-sulfonate are preferred.

Examples of the tetrahydrothiophenium salt include 1-(4-n-butoxynaphthalen-1-yl)tetrahydrothiophenium trifluoromethanesulfonate, 1-(4-n-butoxynaphthalen-1-yl)tetrahydrothiophenium nonafluoro-n-butanesulfonate, 1-(4-n-butoxynaphthalen-1-yl)tetrahydrothiophenium perfluoro-n-octanesulfonate, 1-(4-n-butoxynaphthalen-1-yl)tetrahydrothiophenium 2-bicyclo[2.2.1]hept-2-yl-1,1,2,2-tetrafluoroethanesulfonate, 1-(4-n-butoxynaphthalen-1-yl)tetrahydrothiophenium camphorsulfonate, 1-(6-n-butoxynaphthalen-2-yl)tetrahydrothiophenium trifluoromethanesulfonate, 1-(6-n-butoxynaphthalen-2-yl)tetrahydrothiophenium nonafluoro-n-butanesulfonate, 1-(6-n-butoxynaphthalen-2-yl)tetrahydrothiophenium perfluoro-n-octanesulfonate, 1-(6-n-butoxynaphthalen-2-yl)tetrahydrothiophenium 2-bicyclo[2.2.1]hept-2-yl-1,1,2,2-tetrafluoroethanesulfonate, 1-(6-n-butoxynaphthalen-2-yl)tetrahydrothiophenium camphorsulfonate, 1-(3,5-dimethyl-4-hydroxyphenyl)tetrahydrothiophenium trifluoromethanesulfonate, 1-(3,5-dimethyl-4-hydroxyphenyl)tetrahydrothiophenium nonafluoro-n-butanesulfonate, 1-(3,5-dimethyl-4-hydroxyphenyl)tetrahydrothiophenium perfluoro-n-octanesulfonate, 1-(3,5-dimethyl-4-hydroxyphenyl)tetrahydrothiophenium 2-bicyclo[2.2.1]hept-2-yl-1,1,2,2-tetrafluoroethanesulfonate, 1-(3,5-dimethyl-4-hydroxyphenyl)tetrahydrothiophenium camphorsulfonate, and the like. Among these tetrahydrothiophenium salts, 1-(4-n-butoxynaphthalen-1-yl)tetrahydrothiophenium nonafluoro-n-butanesulfonate, 1-(4-n-butoxynaphthalen-1-yl)tetrahydrothiophenium perfluoro-n-octanesulfonate and 1-(3,5-dimethyl-4-hydroxyphenyl)tetrahydrothiophenium nonafluoro-n-butanesulfonate are preferred.

Examples of the iodonium salt include diphenyliodonium trifluoromethanesulfonate, diphenyliodonium nonafluoro-n- butanesulfonate, diphenyliodonium perfluoro-n-octanesulfonate, diphenyliodonium 2-bicyclo[2.2.1]hept-2-yl-1,1,2,2-tetrafluoroethanesulfonate, diphenyliodonium camphorsulfonate, bis(4-t-butylphenyl)iodonium trifluoromethanesulfonate, bis(4-t-butylphenyl)iodonium nonafluoro-n-butanesulfonate, bis(4-t-butylphenyl)iodonium perfluoro-n-octanesulfonate, bis(4-t-butylphenyl)iodonium 2-bicyclo[2.2.1]hept-2-yl-1,1,2,2-tetrafluoroethanesulfonate, bis(4-t-butylphenyl)iodonium camphorsulfonate, and the like. Among these iodonium salts, bis(4-t-butylphenyl)iodonium nonafluoro-n-butanesulfonate is preferred.

Examples of the sulfonimide compound include N-(trifluoromethanesulfonyloxy)bicyclo[2.2.1]hept-5-ene-2,3-dicarboxyimide, N-(nonafluoro-n-butanesulfonyloxy)bicyclo[2.2.1]hept-5-ene-2,3-dicarboxyimide, N-(perfluoro-n-octanesulfonyloxy)bicyclo[2.2.1]hept-5-ene-2,3-dicarboxyimide, N-(2-bicyclo[2.2.1]hept-2-yl-1,1,2,2-tetrafluoroethanesulfonyloxy)bicyclo[2.2.1]hept-5-ene-2,3-dicarboxyimide, N-(2-(3-tetracyclo[4.4.0.1$^{2,5}$.1$^{7,10}$]dodecanyl)-1,1-difluoroethanesulfonyloxy)bicyclo[2.2.1]hept-5-ene-2,3-dicarboxyimide, N-(camphorsulfonyloxy)bicyclo[2.2.1]hept-5-ene-2,3-dicarboxyimide, and the like. Among these sulfonimide compounds, N-(trifluoromethanesulfonyloxy)bicyclo[2.2.1]hept-5-ene-2, 3-dicarboxyimide is preferred.

These acid generators (B) may be used either alone, or in combination of two or more thereof. The amount of the acid generator (B) employed in the case of the acid generator (B) being the acid generating agent is typically no less than 0.1 parts by mass and no greater than 20 parts by mass, and preferably no less than 0.5 parts by mass and no greater than 15 parts by mass with respect to 100 parts by mass of the polymer (A) in view of ensuring the sensitivity and developability for use as a resist. In this case, when the amount of the acid generating agent (B) employed is less than 0.1 parts by mass, the sensitivity and developability tend to be deteriorated, whereas the amount of the acid generating agent (B) exceeding 15 parts by mass is likely to result in reduction of radiation transmittance, and to render the formation of the desired resist patterns difficult.

Group Represented by the Formula (1)

The composition is characterized by: containing at least two components including the polymer (A) and the acid generator (B); and one or more components of the radiation-sensitive composition having the group represented by the above formula (1). The one or more components having the group represented by the above formula (1) generate(s) an acid at light-exposed sites to enhance an insolubility of the polymer (A) in a developer solution, and as a result, roughness of the surface at light-exposed sites after development is prevented. On the other hand, a more superior acid-capturing function by an anion is exhibited at light-unexposed sites, thereby serving as a quencher, and thus an acid diffused from the light-exposed sites is captured. In other words, the function as a quencher is exhibited only at light-unexposed sites; therefore, a contrast of a deprotecting reaction is improved, and as a result further improvement of a resolution is enabled. The component having a group represented by the formula (1) is acceptable as long as the acid generated upon exposure is relatively weaker than the acid generated from the radiation-sensitive acid generator (B), without a need of having a basic group. It is more preferred that the component having a group represented by the formula (1) has only an acidic group, as compared with the case in which a basic group and an acidic group are both included, since the contrast of the light-exposed site with the light-unexposed site is likely to be produced.

In the formula (1), A$^-$ represents —N$^-$—SO$_2$—R$^D$, —COO$^-$, —O$^-$ or —SO$_3^-$, wherein in a case where A$^-$ represents —SO$_3^-$, —SO$_3^-$ does not directly bond to a carbon atom having a fluorine atom; R$^D$ represents a linear or branched monovalent hydrocarbon group having 1 to 10 carbon atoms or a cyclic monovalent hydrocarbon group having 3 to 20 carbon atoms, wherein a part or all of hydrogen atoms of the hydrocarbon group represented by R$^D$ are not substituted or substituted by a fluorine atom; and X$^+$ represents an onium cation.

Examples of the linear or branched monovalent hydrocarbon group having 1 to 10 carbon atoms represented by R$^D$ include a methyl group, an ethyl group, a propyl group, a butyl group, and the like.

Examples of the cyclic monovalent hydrocarbon group having 3 to 20 carbon atoms represented by R$^D$ include a cyclopentyl group, a cyclohexyl group, a norbornyl group, an adamantyl group, and the like.

A$^-$ preferably bonds to a carbon atom, and the carbon atom preferably does not have an electron-withdrawing group (atom) so as to give an acid relatively weaker than the acid generated from the radiation-sensitive acid generator (B).

Examples of the onium cation represented by X$^+$ include sulfonium cations such as a triphenylsulfonium cation, a 4-cyclohexylphenyldiphenylsulfonium cation, a 4-methanesulfonylphenyldiphenylsulfonium cation and a sulfone group-containing triphenylsulfonium cation represented by the above formula (4);

iodonium cations such as a diphenyliodonium cation and a bis(4-t-butylphenyl)iodonium cation;

tetrahydrothiophenium cations such as a 1-(4-n-butoxynaphthalen-1-yl)tetrahydrothiophenium cation, a 1-(6-n-butoxynaphthalen-2-yl)tetrahydrothiophenium cation and a 1-(3,5-dimethyl-4-hydroxyphenyl)tetrahydrothiophenium cation, and the like.

Of these, sulfonium cations are preferred, and a triphenylsulfonium cation and a sulfone group-containing triphenylsulfonium cation represented by the above formula (4) are more preferred. When the sulfonium cation having the specific structure represented by the above formula (4) is used as the cation represented by X$^+$, dispersibility in the resist coating film is increased, whereby effects of the embodiment of the present invention are particularly improved.

In the formula (4), R$^6$ to R$^8$ each independently represent a hydrogen atom, a halogen atom, a hydroxyl group, an alkyl group having 1 to 10 carbon atoms, a cycloalkyl group having 3 to 12 carbon atoms, or an alkoxy group having 1 to 10 carbon atoms, each not having or having a substituent.

Examples of the halogen atom represented by R$^6$ to R$^8$ include a fluorine atom, a chlorine atom, a bromine atom, an iodine atom, and the like.

Examples of the alkyl group having 1 to 10 carbon atoms represented by R$^6$ to R$^8$ include a methyl group, an ethyl group, a propyl group, a butyl group, and the like.

Examples of the cycloalkyl group having 3 to 12 carbon atoms represented by R$^6$ to R$^8$ include a cyclopentyl group, a cyclohexyl group, a norbornyl group, and the like.

Examples of the alkoxy group having 1 to 10 carbon atoms represented by R$^6$ to R$^8$ include a methoxy group, an ethoxy group, a propoxy group, a butoxy group, and the like.

Specific examples of the sulfone group-containing triphenylsulfonium cation represented by the above formula (4) include 4-cyclohexylsulfonylphenyldiphenylsulfonium cation, and the like cations represented by the following formula.

The manner of inclusion of one or more components having the group represented by the above formula (1) in the composition may be exemplified by:

(i) inclusion as a compound in the form of the compound (C) (hereinafter, referred to as "inclusion mode (i)");

(ii) inclusion in the form of the polymer (A) which further includes a structural unit derived from at least one selected from the group consisting of the compound represented by the above formula (3-1) and the compound represented by the above formula (3-2) (hereinafter, referred to as "inclusion mode (ii)"); and (iii) inclusion in the form of a polymer that includes a structural unit derived from at least one selected from the group consisting of the compound represented by the above formula (3-1) and the compound represented by the above formula (3-2) in the composition, in addition to the polymer (A) (hereinafter, referred to as "inclusion mode (iii)").

Each inclusion mode will be described in detail below.

Inclusion Mode (i)

According to the inclusion mode (i), the composition further contains the compound (C) represented by the above formula (2) in the pattern-forming method. This inclusion mode is advantageous in that the composition can be relatively conveniently prepared.

In the formula (2), $R^1$ represents a hydrogen atom or a monovalent organic group; and $A^-$ and $X^+$ are as defined in the above formula (1).

The monovalent organic group represented by $R^1$ is exemplified by an alkyl group having 1 to 20 carbon atoms, a cycloalkyl group having 3 to 20 carbon atoms, an aryl group having 6 to 30 carbon atoms, an aralkyl group having 7 to 30 carbon atoms, a heterocyclic group having 3 to 30 carbon atoms, and the like. A part or all of hydrogen atoms of these groups are not substituted or substituted. Moreover, an atom that bonds to $A^-$ in $R^1$ is preferably a carbon atom, and the carbon atom preferably does not have an electron-withdrawing group (atom) so as to give the compound (C) as an acid relatively weaker than the acid generated from the radiation-sensitive acid generator (B).

The substituent which may be included in the alkyl group, the cycloalkyl group, the aryl group, the aralkyl group and the heterocyclic group is exemplified by a hydroxyl group, a halogen atom, an alkoxy group, a lactone group, an alkylcarbonyl group, and the like.

Illustrative examples of $X^+$ in the formula (2) include groups similar to those exemplified in the above section "Group Represented by the Formula (1)".

Preferred compound (C) is exemplified by structural units represented by the following formulae.

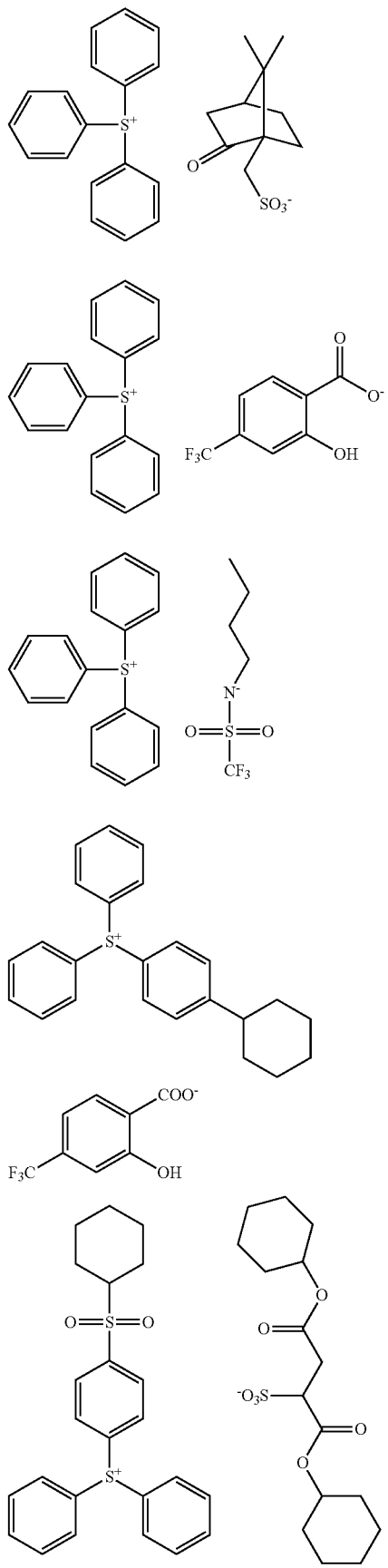

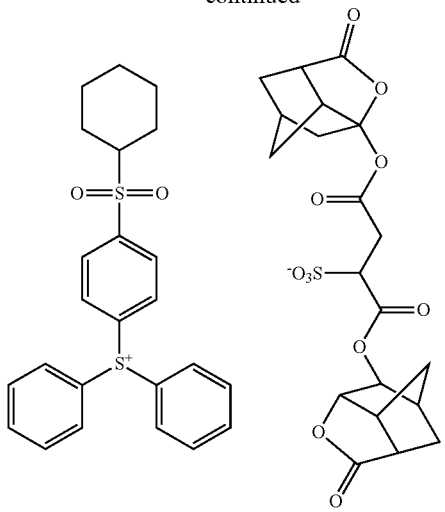

These compounds (C) may be used either alone, or in combination of two or more thereof. In the case in which only the inclusion mode (i) is adopted in the composition, the amount of the compound (C) used is preferably no less than 1 part by mass and no greater than 15 parts by mass, and more preferably no less than 3 parts by mass and no greater than 10 parts by mass with respect to 100 parts by mass of the polymer (A). When the amount of the compound (C) used is less than 1 part by mass, effects of the embodiment of the present invention may not be satisfactorily achieved, involving e.g., impaired suppression of roughness of the surface at light-exposed sites after development, and the like. However, the limitation of the amount of the compound (C) is not applicable to the composition in which a manner of the inclusion mode (ii) and/or the inclusion mode (iii) is adopted in combination with the inclusion mode (i). On the other hand, when the amount exceeds 15 parts by mass, deterioration of the shape of the pattern may be found due to a decrease of sensitivity and a resist transmittance of the composition.

Inclusion Mode (ii)

According to the inclusion mode (ii), the polymer (A) further includes the structural unit (IV) derived from at least one selected from the group consisting of the compound represented by the above formula (3-1) and the compound represented by the above formula (3-2) in the pattern-forming method. This inclusion mode allows the group represented by the above formula (1) to be evenly distributed in the resist film, and thus the effects of the embodiment of the present invention can be still further improved. It is to be noted that the inclusion mode (i) may be adopted in combination with the inclusion mode (ii) and the inclusion mode (iii).

In the formula (3-1), $A^-$ and $X^+$ are as defined in the above formula (1); $R^2$ represents a hydrogen atom, a methyl group or a trifluoromethyl group; $R^3$ and $R^5$ each independently represent a single bond, a linear or branched divalent hydrocarbon group having 1 to 10 carbon atoms, or a divalent hydrocarbon group that includes a cyclic structure and has 3 to 20 carbon atoms, wherein a part or all of hydrogen atoms of these hydrocarbon groups are not substituted or substituted by a fluorine atom, and wherein in a case where $A^-$ represents $-SO_3^-$, $-SO_3^-$ does not directly bond to a carbon atom having a fluorine atom; and $R^4$ represents a single bond, $-O-$, $-C(=O)-$, $-C(=O)-O-$, $-O-C(=O)-$ or a sulfinyl group.

In the formula (3-2), $A^-$ and $X^+$ are as defined in the above formula (1); and $R^{2'}$ represents a hydrogen atom, a methyl group or a trifluoromethyl group.

Examples of the linear or branched divalent hydrocarbon group having 1 to 10 carbon atoms represented by $R^3$ and $R^5$ include a methylene group, an ethylene group, a propylene group, a butylene group, and the like.

Examples of the divalent hydrocarbon group that includes a cyclic structure and has 3 to 20 carbon atoms represented by $R^3$ and $R^5$ include groups derived by removing two hydrogen atoms from an alicyclic hydrocarbon such as cyclopropane, cyclobutane, cyclopentane, cyclohexane, dicyclopentane, norbornane, tricyclodecane, tetracyclododecane or adamantane.

Illustrative examples of $X^+$ in the formulae (3-1) and (3-2) include groups similar to those exemplified in the above section "Group Represented by the Formula (1)".

The monomer that gives the structural unit (IV) is exemplified by compounds represented by following formulae.

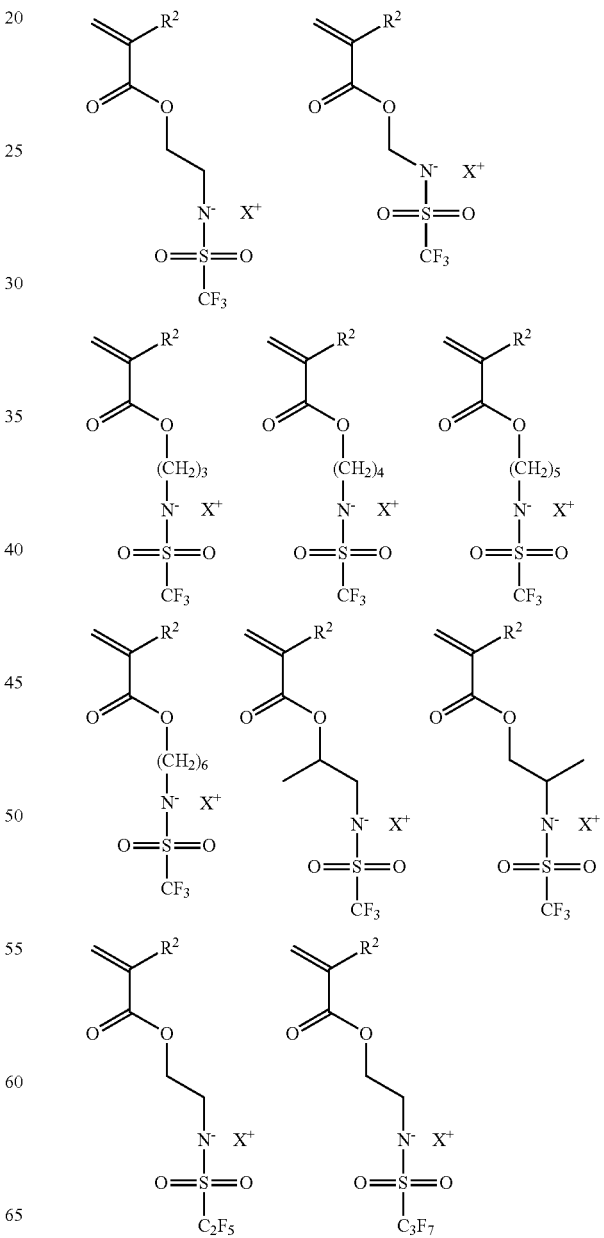

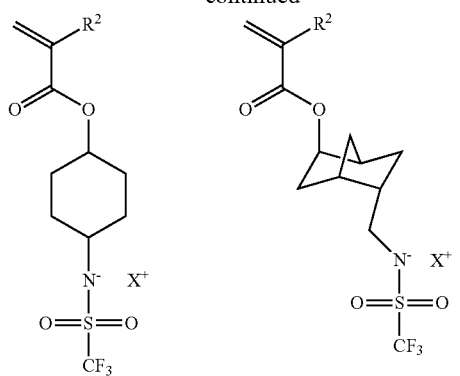
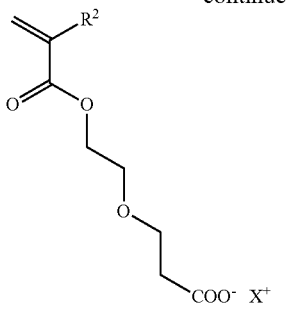
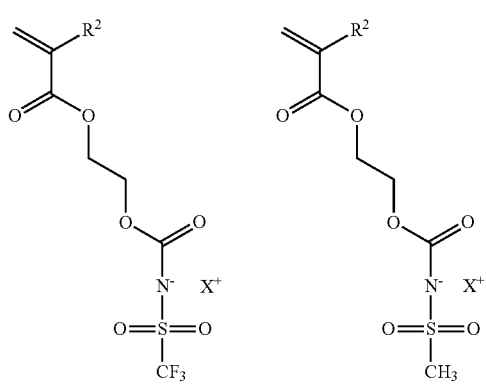
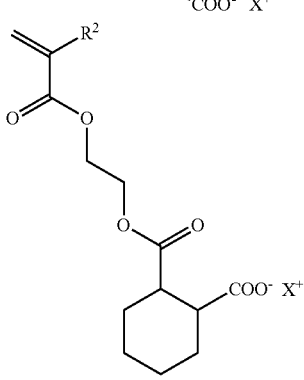
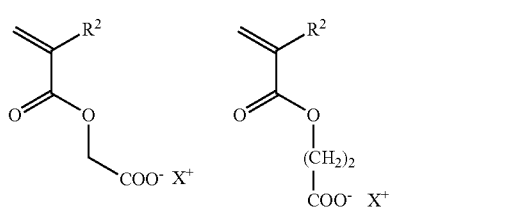
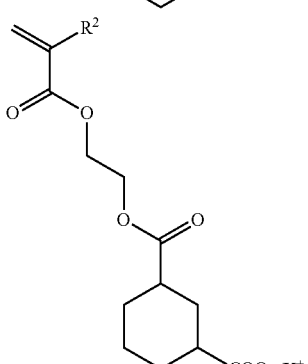
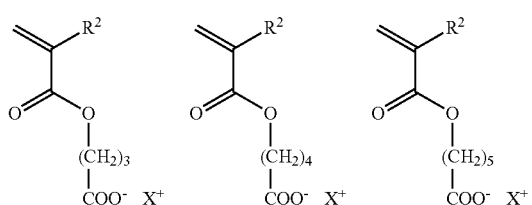
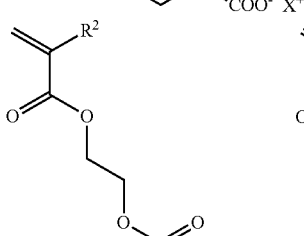
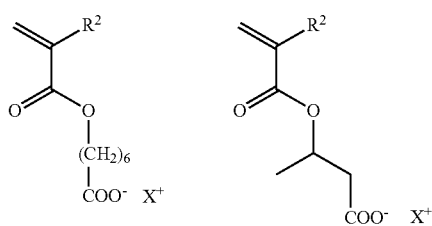
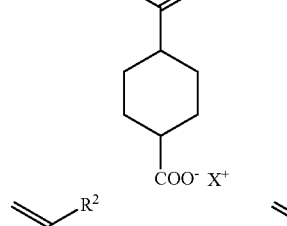
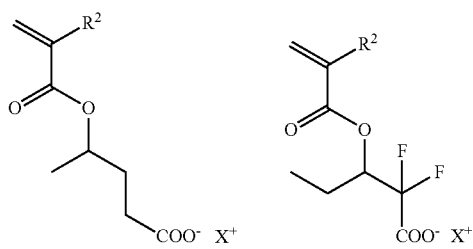
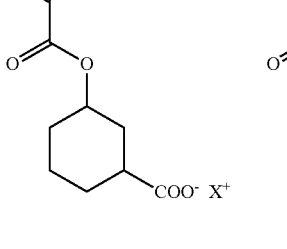

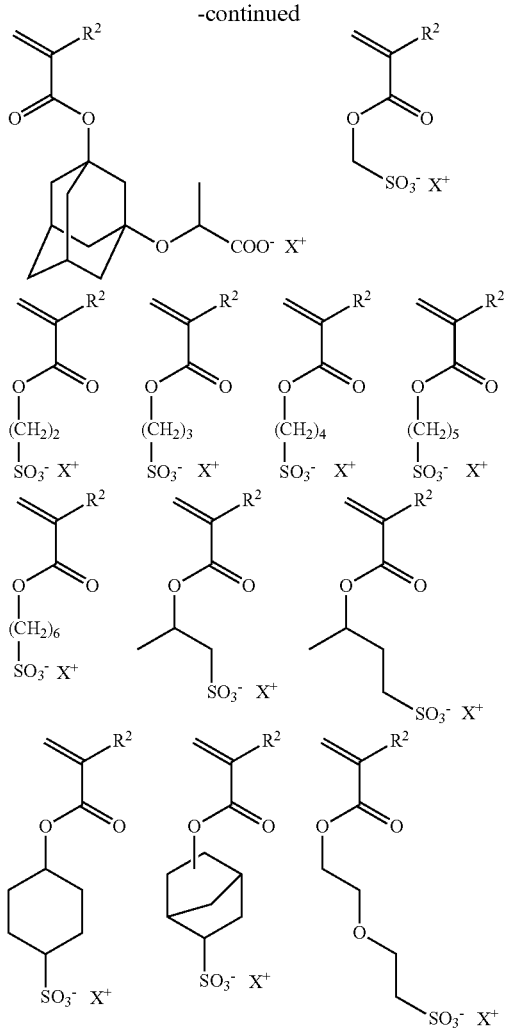

The polymer (A) may include either one type alone, or two or more types of the structural unit (IV). In the case in which only the inclusion mode (ii) is adopted in the composition, the proportion of the structural unit (IV) contained in the polymer (A) is preferably 0.5 mol % to 20 mol %, and more preferably 1 mol % to 10 mol % with respect to the entire structural units constituting the polymer (A). When the proportion of the structural unit (I) contained falls within the above range, the effects of the embodiment of the present invention can be satisfactorily achieved.

Inclusion Mode (iii)

According to the inclusion mode (iii), the composition further contains the polymer (D) that includes the structural unit derived from at least one selected from the group consisting of the compound represented by the above formula (3-1) and the compound represented by the above formula (3-2) in the pattern-forming method. An explanation of details of the formulae (3-1) and (3-2) is omitted in this section since the explanation in connection with the inclusion mode (ii) above is applicable.

The polymer (D) may include either one type alone, or two or more types of the structural unit (IV). In the case in which only the inclusion mode (iii) is adopted in the composition, the content of the polymer (D) in the radiation-sensitive composition is preferably no less than 20% by mass, and more preferably no less than 30% by mass with respect to 100 parts by mass of the polymer (A). When the content of the polymer (D) in the radiation-sensitive composition falls within the above range, the effects of the embodiment of the present invention can be satisfactorily achieved.

Optional Component

In addition to the essential components described in the foregoing, the radiation-sensitive composition may contain a fluorine atom-containing polymer, a nitrogen-containing compound, a solvent, a surfactant, an alicyclic skeleton-containing compound, a sensitizing agent and the like as optional components within a range not leading to impairment of the effects of the embodiment of the present invention. These optional components will be described in detail below. These optional components may be used either alone, or as a mixture of two or more thereof. In addition, the amount of the other optional component blended may be appropriately decided to meet the purpose thereof.

Fluorine Atom-Containing Polymer

The radiation-sensitive composition may contain a fluorine atom-containing polymer (excluding the polymer (A)). When the radiation-sensitive composition contains the fluorine atom-containing polymer, in forming a resist film, the fluorine atom-containing polymer tends to be unevenly distributed in the vicinity of the surface of the resist film due to oil repellent characteristic feature of the fluorine atom-containing polymer in the film. Thus, elution of an acid generating agent, an acid diffusion control agent and the like into a liquid immersion medium can be prevented in liquid immersion lithography. In addition, owing to a water repellent feature of the fluorine atom-containing polymer, an advancing contact angle of a liquid immersion medium on a resist film can be controlled to fall within a desired range, whereby formation of bubble defects can be suppressed. Furthermore, a higher receding contact angle of a liquid immersion medium on a resist film is attained, thereby enabling exposure by high-speed scanning without remaining water droplets. The radiation-sensitive composition containing the fluorine atom-containing polymer in this manner allows a resist coating film suited for liquid immersion lithography process to be formed.

The fluorine-containing polymer is not particularly limited as long as a fluorine atom is included, and preferably has a content of fluorine atoms (% by mass) grater than that of the polymer (A). When the content of fluorine atoms of the fluorine-containing polymer is greater than that of the polymer (A), a higher degree of the uneven distribution is attained, whereby characteristics such as water repellency and suppressive properties on elution of the resultant resist coating film can are improved.

The fluorine atom-containing polymer in the embodiment of the present invention is prepared by polymerizing one or more types of monomers that include a fluorine atom in the structure thereof.

The monomers that give a polymer that includes a fluorine atom in the structure thereof are exemplified by a monomer that includes a fluorine atom in its main chain, a monomer that includes a fluorine atom in its side chain, and a monomer that includes a fluorine atom in its main chain and side chain.

Examples of the monomer that gives a polymer that includes a fluorine atom in its main chain include α-fluoroacrylate compounds, α-trifluoromethyl acrylate compounds, β-fluoroacrylate compounds, β-trifluoromethyl acrylate compounds, α,β-fluoroacrylate compounds, α,β-trifluoromethyl acrylate compounds, compounds derived by substituting hydrogen(s) of one or more types of vinyl moieties by fluorine or a trifluoromethyl group, etc., and the like.

Examples of the monomer that gives a polymer that includes a fluorine atom in its side chain include compounds in which an alicyclic olefin compound such as norbornene has fluorine, a fluoroalkyl group and/or a derivative thereof as a side chain, ester compounds of acrylic acid or methacrylic acid with a fluoroalkyl group and/or a derivative thereof, olefins having a fluorine atom, a fluoroalkyl group and/or a derivative thereof as one or more types of side chain (a site excluding a double bond), and the like.

Examples of the monomer that gives a polymer that includes a fluorine atom in its main chain and side chain include ester compounds of α-fluoroacrylic acid, β-fluoroacrylic acid, α,β-fluoroacrylic acid, α-trifluoromethyl acrylic acid, β-trifluoromethyl acrylic acid, α,β-trifluoromethylacryli acid or the like with a fluoroalkyl group and/or a derivative thereof, compounds derived by substituting hydrogen(s) of one or more types of vinyl moieties by a fluorine atom or a trifluoromethyl group and substituting a side chain of the compound with a fluorine atom, a fluoroalkyl group and/or a derivative thereof; alicyclic olefin compounds derived by substituting hydrogen(s) bonded to one or more types of double bonds by a fluorine atom or a trifluoromethyl group, etc., and having a fluorinated alkyl group and/or a derivative thereof as a side chain; and the like. The alicyclic olefin compound as referred to herein means a compound that includes a double bond in a part of its ring.

The structural unit included in the fluorine atom-containing polymer is exemplified by a structural unit represented by the following formula (hereinafter, may be also referred to as "structural unit (V)").

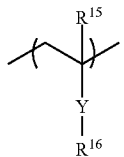

In the above formula, $R^{15}$ represents a hydrogen, a methyl group or a trifluoromethyl group; Y represents a linking group; $R^{16}$ represents a linear or branched alkyl group having 1 to 6 carbon atoms or a monovalent alicyclic hydrocarbon group having 4 to 20 carbon atoms or a derivative thereof having at least one or more fluorine atoms.

Examples of the linking group represented by Y include a single bond, an oxygen atom, a sulfur atom, a carbonyloxy group, an oxycarbonyl group, an amide group, a sulfonylamide group, a urethane group, and the like.

Examples of the monomer that gives the structural unit (V) include (meth)acrylic acid trifluoromethyl ester, (meth)acrylic acid 2,2,2-trifluoroethyl ester, (meth)acrylic acid perfluoroethyl ester, (meth)acrylic acid perfluoro-n-propyl ester, (meth)acrylic acid perfluoro-i-propyl ester, (meth)acrylic acid perfluoro-n-butyl ester, (meth)acrylic acid perfluoro-i-butyl ester, (meth)acrylic acid perfluoro-t-butyl ester, (meth)acrylic acid 2-(1,1,1,3,3,3-hexafluoropropyl)ester, (meth)acrylic acid 1-(2,2,3,3,4,4,5,5-octafluoropentyl)ester, (meth)acrylic acid perfluorocyclohexylmethyl ester, (meth)acrylic acid 1-(2,2,3,3,3-pentafluoropropyl)ester, (meth)acrylic acid 1-(3,3,4,4,5,5,6,6,7,7,8,8,9,9,10,10,10-heptadecafluorodecyl)ester, (meth)acrylic acid 1-(5-trifluoromethyl-3,3,4,4,5,6,6,6-octafluorohexyl)ester, and the like.

The fluorine atom-containing polymer may contain either one type alone, or two or more types of the structural unit (V). The proportion of the structural unit (V) contained is typically no less than 5 mol %, preferably no less than 10 mol %, and more preferably no less than 15 mol % with respect to 100 mol % of the entire structural units in the fluorine atom-containing polymer. When the proportion of the structural unit (V) is less than 5 mol %, a receding contact angle of no less than 70° may not be achieved, and/or elution of the acid generating agent and the like from the resist coating film may not be suppressed.

In addition to the structural unit (V), the fluorine atom-containing polymer may include at least one type of "other structural units" such as, for example: in order to control rates of dissolution in developer solutions, a structural unit having an acid-labile group, a structural unit having a lactone skeleton, a hydroxyl group, a carboxyl group or the like, a structural derived from an alicyclic compound; and/or a structural unit derived from an aromatic compound for inhibiting scattering by reflection of light from the substrate.

The other structural unit having an acid-labile group is exemplified by a similar one to the structural unit (I). The other structural unit having a lactone skeleton is exemplified by a similar one to the structural unit (II). The other structural unit having a hydroxyl group is exemplified by a similar one to the structural unit (III).

The other structural unit derived from an alicyclic compound (hereinafter, may be referred to as "structural unit (VI)") is exemplified by a structural unit represented by the following formula.

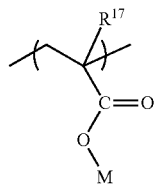

In the above formula, $R^{17}$ represents a hydrogen atom, a methyl group, or a trifluoromethyl group; and M represents an alicyclic hydrocarbon group having 4 to 20 carbon atoms.

The alicyclic hydrocarbon group having 4 to 20 carbon atoms is exemplified by hydrocarbon groups having an alicyclic ring derived from a cycloalkane such as cyclobutane, cyclopentane, cyclohexane, bicyclo[2.2.1]heptane, bicyclo[2.2.2]octane, tricyclo[5.2.1.0$^{2,6}$]decane, tetracyclo[6.2.1.1$^{3,6}$.0$^{2,7}$]dodecane or tricyclo[3.3.1.1$^{3,7}$]decane. The alicyclic ring derived from a cycloalkane may have a substituent, and may be substituted with at least one type or one of linear, branched or cyclic alkyl groups having 1 to 4 carbon atoms such as, for example, a methyl group, an ethyl group, a n-propyl group, an i-propyl group, a n-butyl group, a 2-methylpropyl group, a 1-methylpropyl group and a t-butyl group.

Examples of the monomer that gives the structural unit (VI) include (meth)acrylic acid bicyclo[2.2.1]hept-2-yl ester, (meth)acrylic acid bicyclo[2.2.2]oct-2-yl ester, (meth)acrylic acid tricyclo[5.2.1.0$^{2,6}$]dec-7-yl ester, (meth)acrylic acid tetracyclo[6.2.1.1$^{3,6}$.0$^{2,7}$]dodec-9-yl ester, (meth)acrylic acid tricyclo[3.3.1.1$^{3,7}$]dec-1-yl ester, (meth)acrylic acid tricyclo[3.3.1.1$^{3,7}$]dec-2-yl ester, and the like.

Examples of preferred monomer that yields the other structural unit derived from the aromatic compound include styrene, α-methylstyrene, 2-methylstyrene, 3-methylstyrene, 4-methylstyrene, 2-methoxystyrene, 3-methoxystyrene, 4-methoxystyrene, 4-(2-t-butoxycarbonylethyloxy)styrene, 2-hydroxystyrene, 3-hydroxystyrene, 4-hydroxystyrene, 2-hydroxy-α-methylstyrene, 3-hydroxy-α-methylstyrene, 4-hydroxy-α-methylstyrene, 2-methyl-3-hydroxystyrene, 4-methyl-3-hydroxystyrene, 5-methyl-3-hydroxystyrene, 2-methyl-4-hydroxystyrene, 3-methyl-4-hydroxystyrene, 3,4-dihydroxystyrene, 2,4,6-trihydroxystyrene, 4-t-butoxystyrene, 4-t-butoxy-α-methylstyrene, 4-(2-ethyl-2-propoxy) styrene, 4-(2-ethyl-2-propoxy)-α-methylstyrene, 4-(1-ethoxyethoxy)styrene, 4-(1-ethoxyethoxy)-α-methylstyrene, phenyl(meth)acrylate, benzyl(meth)acrylate, acenaphthylene, 5-hydroxyacenaphthylene, 1-vinylnaphthalene, 2-vinylnaphthalene, 2-hydroxy-6-vinylnaphthalene, 1-naphthyl(meth)acrylate, 2-naphthyl(meth)acrylate, 1-naphthylmethyl(meth)acrylate, 1-anthryl(meth)acrylate, 2-anthryl(meth)acrylate, 9-anthryl(meth)acrylate, 9-anthrylmethyl(meth)acrylate, 1-vinylpyrene, and the like.

The proportion of the other structural unit contained is typically no greater than 80 mol %, preferably no greater than mol %, and more preferably no greater than 70 mol % with respect to 100 mol % of the entire structural units in the fluorine atom-containing polymer.

The Mw of the fluorine atom-containing polymer is preferably 1,000 to 50,000, more preferably 1,000 to 30,000, and particularly preferably 1,000 to 10,000. When the Mw of the fluorine atom-containing polymer is less than 1,000, it is impossible to attain a sufficient advancing contact angle. On the other hand, the Mw of fluorine atom-containing the polymer exceeding 50,000 is likely to result in deteriorated developability of the resultant resist.

The ratio (Mw/Mn) of the Mw to the Mn of the fluorine atom-containing polymer is typically 1 to 3, and preferably 1 to 2.

The proportion of the fluorine atom-containing polymer contained in the radiation-sensitive composition is preferably 0 to 50 parts by mass, more preferably 0 to 20 parts by mass, still more preferably 1 to 10 parts by mass, and particularly preferably 2 to 8 parts by mass with respect to 100 parts by mass of the polymer (A). When the proportion of the fluorine atom-containing polymer contained in the radiation-sensitive composition falls within the above range, water repellency and elution inhibitory properties of the surface of the resultant resist coating film can be further improved.

Synthesis Method of Fluorine Atom-Containing Polymer

The fluorine atom-containing polymer may be synthesized, for example, by polymerizing the monomer corresponding to each predetermined structural unit in an appropriate solvent using a radical polymerization initiator.

The solvent for use in the polymerization may include, for example, those exemplified in the synthesis method of the polymer (A).

The reaction temperature in the polymerization is typically 40° C. to 150° C., and preferably 50° C. to 120° C. The reaction time is typically 1 hour to 48 hrs, and preferably 1 hour to 24 hrs.

Nitrogen-Containing Compound

The nitrogen-containing compound exerts the effect of controlling diffusion phenomenon of the acid generated from the acid generator (B) upon the exposure in the resist coating film, and suppressing unfavorable chemical reactions in unexposed regions; as a result, storage stability of the resultant radiation-sensitive composition is further improved, and resolution of the resist is further improved, while suppressing variation of line width of the resist pattern caused by variation of post-exposure delay (PED) from the exposure until a development treatment, which enables the radiation-sensitive resin composition with superior process stability to be obtained. The mode of incorporation of the nitrogen-containing compound into the composition may be in a free compound form or in an incorporated form as a part of the polymer, or in both of these forms.

The nitrogen-containing compound is exemplified by an amine compound, an amide group-containing compound, a urea compound, a nitrogen-containing heterocyclic compound, and the like.

Examples of the amine compound include mono(cyclo)alkylamines; di(cyclo)alkylamines; tri(cyclo)alkylamines; substituted alkylaniline or derivatives thereof; ethylenediamine, N,N,N',N'-tetramethylethylenediamine, tetramethylenediamine, hexamethylenediamine, 4,4'-diaminodiphenylmethane, 4,4'-diaminodiphenyl ether, 4,4'-diaminobenzophenone, 4,4'-diaminodiphenylamine, 2,2-bis(4-aminophenyl)propane, 2-(3-aminophenyl)-2-(4-aminophenyl)propane, 2-(4-aminophenyl)-2-(3-hydroxyphenyl)propane, 2-(4-aminophenyl)-2-(4-hydroxyphenyl)propane, 1,4-bis(1-(4-aminophenyl)-1-methylethyl)benzene, 1,3-bis(1-(4-aminophenyl)-1-methylethyl)benzene, bis(2-dimethylaminoethyl)ether, bis(2-diethylaminoethyl)ether, 1-(2-hydroxyethyl)-2-imidazolidinone, 2-quinoxalinol, N,N,N',N'-tetrakis(2-hydroxypropyl)ethylenediamine, N,N,N',N''N''-pentamethyldiethylenetriamine, and the like.

Examples of the amide group-containing compound include N-t-butoxycarbonyl group-containing amino compounds, formamide, N-methylformamide, N,N-dimethylformamide, acetamide, N-methylacetamide, N,N-dimethylacetamide, propionamide, benzamide, pyrrolidone, N-methylpyrrolidone, N-acetyl-1-adamantylamine, tris(2-hydroxyethyl)isocyanurate, and the like.

Examples of the urea compound include urea, methylurea, 1,1-dimethylurea, 1,3-dimethylurea, 1,1,3,3-tetramethylurea, 1,3-diphenylurea, tri-n-butylthiourea, and the like.

Examples of the nitrogen-containing heterocyclic compound include imidazoles; pyridines; piperazines; pyrazine, pyrazole, pyridazine, quinoxaline, purine, pyrrolidine, piperidine, piperidine ethanol, 3-piperidino-1,2-propanediol, morpholine, 4-methylmorpholine, 1-(4-morpholinyl)ethanol, 4-acetylmorpholine, 3-(N-morpholino)-1,2-propanediol, 1,4-dimethylpiperazine, 1,4-diazabicyclo[2.2.2]octane, and the like.

The content of the nitrogen-containing compound is preferably less than 5 parts by mass with respect to 100 parts by mass of the polymer (A). When the total amount of the nitrogen-containing compound used exceeds 5 parts by mass, sensitivity as a resist tends to be deteriorated.

Solvent

The composition typically contains a solvent. The solvent is not particularly limited as long as the solvent can dissolve at least the polymer (A), the acid generator (B), and other optional components added as required. The solvent is exemplified by an alcohol solvent, a ketone solvent, an amide solvent, an ether solvent, an ester solvent and a mixed solvent thereof, and the like. Specific examples of the alcohol solvent, the ketone solvent, the amide solvent, the ether solvent and the ester solvent include solvents similar to each of the solvents exemplified as the organic solvents which may be used for a developer solution in the step (3) of the pattern-forming method.

Examples of the other solvent include aliphatic hydrocarbon solvents such as n-pentane, iso-pentane, n-hexane, iso-hexane, n-heptane, iso-heptane, 2,2,4-trimethylpentane, n-octane, iso-octane, cyclohexane and methylcyclohexane;

aromatic hydrocarbon solvents such as benzene, toluene, xylene, mesitylene, ethylbenzene, trimethylbenzene, methylethylbenzene, n-propylbenzene, iso-propylbenzene, diethylbenzene, iso-butylbenzene, triethylbenzene, di-iso-propylbenzene and n-amylnaphthalene;

halogen-containing solvent such as dichloromethane, chloroform, fluorocarbon, chlorobenzene and dichlorobenzene; and the like.

Of these solvents, propylene glycol monomethyl ether acetate, cyclohexanone, and γ-butyrolactone are preferred.

Surfactant

The surfactant is a component which has effects of improving coating properties, striation, developability, and the like.

Alicyclic Skeleton Compound

The alicyclic skeleton compound is a component which has effects of further improving dry-etching resistance, pattern configuration, adhesiveness to substrates, and the like.

Sensitizing Agent

The sensitizing agent absorbs energy of a radioactive ray and transmits the energy to an acid generating agent, thereby exhibiting an action of increasing the amount of the acid produced, and thus has an effect of improving "apparent sensitivity" of the composition.

Preparation Method of Radiation-Sensitive Composition

The composition may be prepared by, for example, mixing the polymer (A), the acid generator (B), and the optional component(s) in an organic solvent at a predetermined ratio. Also, the composition can be prepared in a state of being dissolved or dispersed in an appropriate organic solvent. The organic solvent is not particularly limited as long as it is one exemplified as the solvent described above, and can dissolve or disperse the polymer (A), the acid generator (B) and the optional component(s). The radiation-sensitive composition is usually prepared upon use by dissolving in a solvent, followed by filtration through a filter having a pore size of, for example, about 0.2 μm.

EXAMPLES

Hereinafter, the present invention will be explained specifically by way of Examples, but the present invention is not limited to the Examples.

Synthesis of Polymer (A)

Monomers used for syntheses of the polymer (A) and fluorine atom-containing polymers described later are shown in the following.

(M-1)
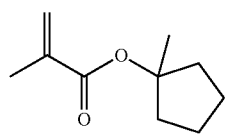

(M-2)
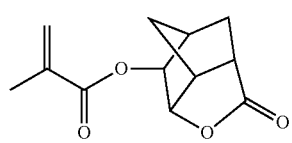

(M-3)
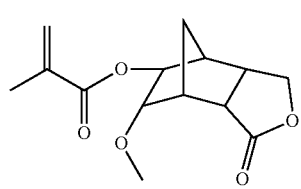

-continued (M-4)
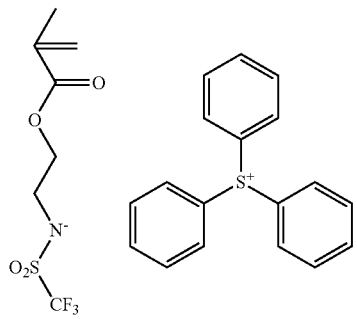

(M-5)
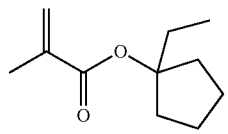

(M-6)
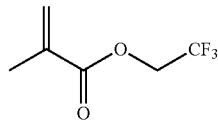

(M-7)
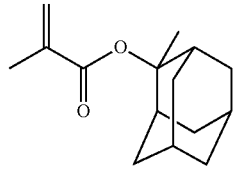

(M-8)
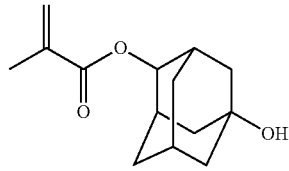

(M-9)
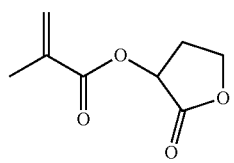

(M-10)
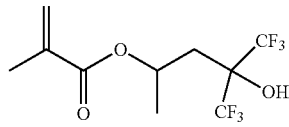

(M-11)
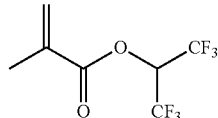

Synthesis Example 1

A monomer solution was prepared by dissolving 12.9 g (50 mol %) of the compound (M-1) and 17.1 g (50 mol %) of the compound (M-2) in 60 g of 2-butanone, and further adding 1.3 g dimethylazobisisobutyronitrile thereto. On the other hand, a 200 mL three-necked flask charged with 30 g of 2-butanone was purged with nitrogen for 30 minutes, and thereafter the reaction vessel was heated to 80° C. with stirring. The monomer solution prepared beforehand was added dropwise using a dropping funnel over 3 hrs. The time when dropwise addition was started was assumed to be a start time point of polymerization and the polymerization reaction was carried out for 6 hours. After completion of the polymerization, the polymerization solution was cooled to no greater than 30° C. by water-cooling and the polymerization solution was charged into 600 g of methanol. The white powder precipitated was filtered off. Thus resultant white powder was washed twice with 150 g of methanol in the state of slurry, and thereafter filtered off and dried at 50° C. for 17 hrs to obtain a copolymer (A-1) as a white powder (yield: 78.5%). The Mw and the Mw/Mn of the copolymer (A-1) were 6,800 and 1.38, respectively. In addition, a result of a $^{13}$C-NMR analysis indicated that a ratio of proportions of structural units derived from the compound (M-1) and the compound (M-2) was 47.5:52.5 (mol %) in the copolymer (A-1). The $^{13}$C-NMR analysis was carried out using "JNM-EX270" (JEOL Ltd.).

Synthesis Example 2

A monomer solution was prepared by dissolving 11.6 g (50 mol %) of the compound (M-1) and 18.4 g (50 mol %) of the compound (M-3) in 60 g of 2-butanone, and further adding 1.1 g dimethylazobisisobutyronitrile thereto. On the other hand, a 200 mL three-necked flask charged with 30 g of 2-butanone was purged with nitrogen for 30 minutes, and thereafter the reaction vessel was heated to 80° C. with stirring. The monomer solution prepared beforehand was added dropwise using a dropping funnel over 3 hrs. The time when dropwise addition was started was assumed to be a start time point of polymerization and the polymerization reaction was carried out for 6 hours. After completion of the polymerization, the polymerization solution was cooled to no greater than 30° C. by water-cooling and the polymerization solution was charged into 600 g of methanol. The white powder precipitated was filtered off. Thus resultant white powder was washed twice with 150 g of methanol in the state of slurry, and thereafter filtered off and dried at 50° C. for 17 hrs to obtain a copolymer (A-2) as a white powder (yield: 78.5%). The Mw and the Mw/Mn of the copolymer (A-2) were 7,000 and 1.40, respectively. In addition, a result of a $^{13}$C-NMR analysis indicated that a ratio of proportions of structural units derived from the compound (M-1) and the compound (M-3) was 48.5:51.5 (mol %) in the copolymer (A-2).

Synthesis Example 3

A monomer solution was prepared by dissolving 12.2 g (50 mol %) of the compound (M-1), 14.8 g (46 mol %) of the compound (M-2) and 3.0 g (4 mol %) of the compound (M-4) in 60 g of 2-butanone, and further adding 1.3 g dimethylazobisisobutyronitrile thereto. On the other hand, a 200 mL three-necked flask charged with 30 g of 2-butanone was purged with nitrogen for 30 minutes, and thereafter the reaction vessel was heated to 80° C. with stirring. The monomer solution prepared beforehand was added dropwise using a dropping funnel over 3 hrs. The time when dropwise addition was started was assumed to be a start time point of polymerization and the polymerization reaction was carried out for 6 hours. After completion of the polymerization, the polymerization solution was cooled to no greater than 30° C. by water-cooling and the polymerization solution was charged into 600 g of a 1:1 mixed solvent of isopropyl alcohol and hexane. The white powder precipitated was filtered off. Thus resultant white powder was washed twice with 150 g of methanol in the state of slurry, and thereafter filtered off and dried at 50° C. for 17 hrs to obtain a copolymer (A-3) as a white powder (yield: 78.5%). The Mw and the Mw/Mn of the copolymer (A-3) were 7,000 and 1.40, respectively. In addition, a result of a $^{13}$C-NMR analysis indicated that a ratio of proportions of structural units derived from the compound (M-1), the compound (M-2) and the compound (M-4) was 49.9:46.4:3.8 (mol %) in the copolymer (A-3).

Synthesis Example 4

A monomer solution was prepared by dissolving 10.5 g (40 mol %) of the compound (M-1), 3.6 g (10 mol %) of the compound (M-7), 3.7 g (10 mol %) of the compound (M-8), 6.9 g (20 mol %) of the compound (M-2) and 5.3 g (20 mol %) of the compound (M-9) in 60 g of 2-butanone, and further adding 1.3 g dimethylazobisisobutyronitrile thereto. On the other hand, a 200 mL three-necked flask charged with 30 g of 2-butanone was purged with nitrogen for 30 minutes, and thereafter the reaction vessel was heated to 80° C. with stirring. The monomer solution prepared beforehand was added dropwise using a dropping funnel over 3 hrs. The time when dropwise addition was started was assumed to be a start time point of polymerization and the polymerization reaction was carried out for 6 hours. After completion of the polymerization, the polymerization solution was cooled to no greater than 30° C. by water-cooling and the polymerization solution was charged into 600 g of a 1:1 mixed solvent of isopropyl alcohol and hexane. The white powder precipitated was filtered off. Thus resultant white powder was washed twice with 150 g of methanol in the state of slurry, and thereafter filtered off and dried at 50° C. for 17 hrs to obtain a copolymer (A-4) as a white powder (yield: 76.5%). The Mw and the Mw/Mn of the copolymer (A-4) were 7,200 and 1.40, respectively. In addition, a result of a $^{13}$C-NMR analysis indicated that a ratio of proportions of structural units derived from the compound (M-1), the compound (M-7), the compound (M-8) and the compound (M-2) was 38.8:8.9:10.1:21.0:21.2 (mol %) in the copolymer (A-4).

Synthesis of Fluorine Atom-Containing Polymer

Synthesis Example 5

A monomer solution was prepared by dissolving 35.8 g (70 mol %) of the compound (M-5) and 14.2 g (30 mol %) of the compound (M-6) in 100 g of 2-butanone, and further adding 3.2 g of dimethyl-2,2'-azobisisobutyrate thereto. A 500 mL three-necked flask charged with 100 g of 2-butanone was purged with nitrogen for 30 minutes, and thereafter the reaction vessel was heated to 80° C. with stirring. The monomer solution prepared was added dropwise using a dropping funnel over 3 hrs. The time when dropwise addition was started was assumed to be a start time point of a polymerization reaction and the polymerization reaction was carried out for 6 hours. After completion of the polymerization reaction, the polymerization solution was cooled to no greater than 30° C. by water-cooling and the solvent was washed with 825 g of a 2:1:8 mixed solvent of methanol, 2-butanone and hexane, followed by replacement of the solvent with propylene glycol monomethyl ether acetate to obtain a solution of a copolymer (F-1) (38.0 g in terms of solid content, yield: 76%). The Mw and the Mw/Mn of the copolymer (F-1) were 7,000 and 1.40, respectively. A result of a $^{13}$C-NMR analysis indicated that a ratio of proportions of structural units derived from the compound (M-5) and the compound (M-6) was 70.2:29.8 (mol %) in the copolymer (F-1).

Synthesis Example 6

A monomer solution was prepared by dissolving 34.81 g (30 mol %) of the compound (M-10) and 65.19 g (70 mol %) of the compound (M-11) in 100 g of 2-butanone, and further adding 10.35 g of dimethyl-2,2'-azobisisobutyrate thereto. A 1,000 mL three-necked flask charged with 100 g of 2-butanone was purged with nitrogen for 30 minutes, and thereafter the reaction vessel was heated to 80° C. with stirring. The monomer solution prepared was added dropwise using a dropping funnel over 3 hrs. The time when dropwise addition was started was assumed to be a start time point of a polymerization reaction and the polymerization reaction was carried out for 6 hours. After completion of the polymerization reaction, the polymerization solution was cooled to no greater than 30° C. by water-cooling. The reaction solution was transferred to a 4 L separating funnel and then homogeneously diluted with 300 g of n-hexane. Thereto was added 1,200 g of methanol the components were mixed. Next, 60 g of distilled water was poured and the mixture was further stirred, and allowed to stand for 30 minutes. Thereafter, the lower layer was collected, and a propylene glycol monomethyl ether acetate solution was prepared (yield: 62%). The Mw and the Mw/Mn of the polymer (F-2) thus obtained Mw were 7,080 and 1.89, respectively, and the content of low-molecular weight components was 0.07% by mass. In addition, a result of a $^{13}$C-NMR analysis indicated that a ratio of proportions of structural units derived from the compound (M-10) and the compound (M-11) was 29.8:70.2 (mol %) in the polymer (F-2).

Preparation of Radiation-Sensitive Composition

The acid generating agent (B), the compound (C), a nitrogen-containing compound and solvents used for preparation of radiation-sensitive compositions are shown in the following.

Acid Generating Agent (B)

B-1: triphenylsulfonium 1,1,2,2-tetrafluoro-6-(1-adamantanecarbonyloxy)-hexane-1-sulfonate represented by the following formula Compound (C)

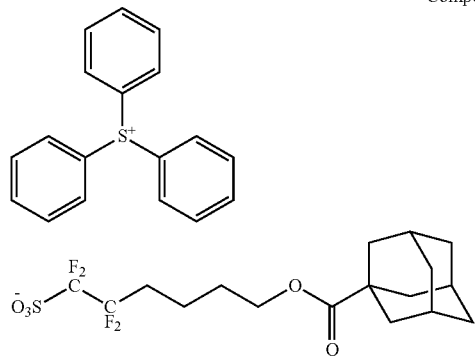

C-1 to C-5: compounds represented by the following formulae (C-1)

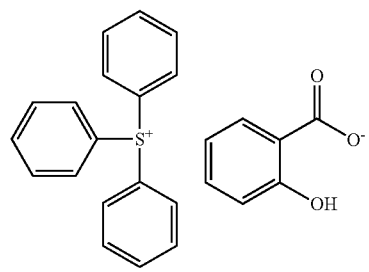

(C-2)

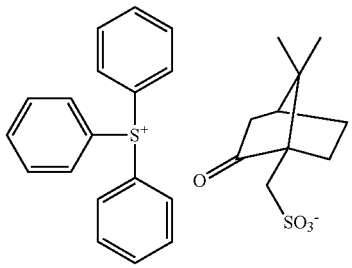

(C-3)

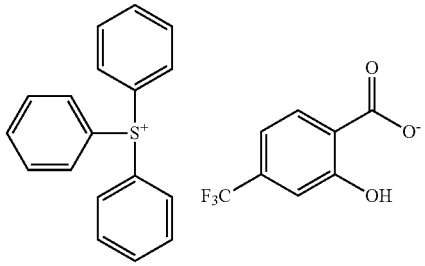

(C-4)

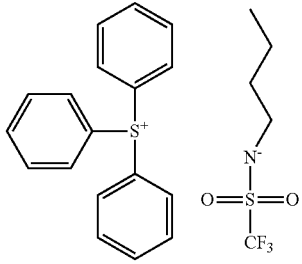

(C-5)

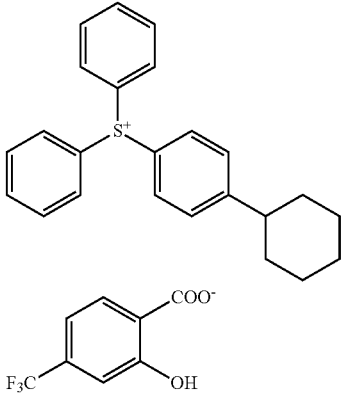

(C-6)

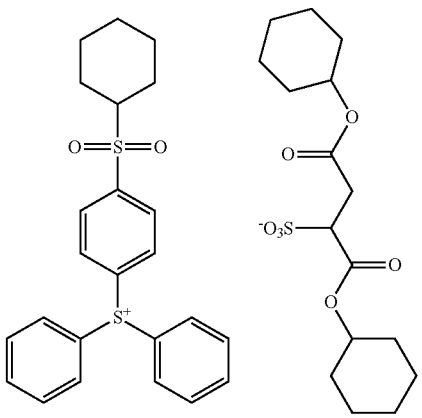

-continued (C-7)

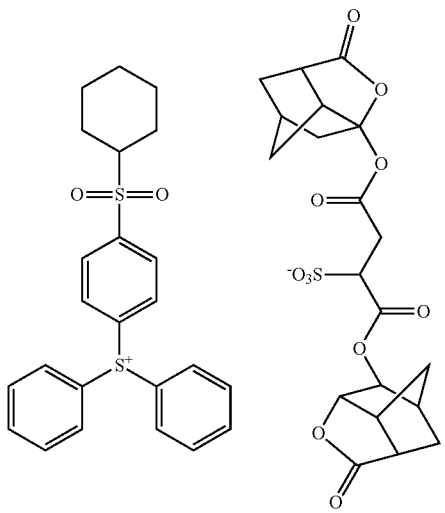

Nitrogen-Containing Compound
D-1: a compound represented by the following formula

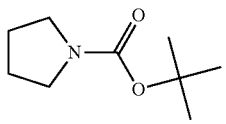

Solvent

E-1: propylene glycol monomethyl ether acetate

E-2: cyclohexanone

E-3: γ-butyrolactone

Example 1

A radiation-sensitive composition (S-1) was prepared by mixing 100 parts by mass of the polymer (A-1), 12.1 parts by mass of the acid generating agent (B-1), 5.0 parts by mass of the compound (C-1), 3 parts by mass of the fluorine atom-containing polymer (F-1), and 1,870 parts by mass of the solvent (E-1), 800 parts by mass of the solvent (E-2) and 30 parts by mass of the solvent (E-3), followed by filtering the resultant mixed solution through a filter with a pore size of 0.2 μm.

Examples 2 to 21 and Comparative Examples 1 to 2

Radiation-sensitive compositions were prepared in a similar manner to Example 1 except that each of the type and the amount shown in Tables 1-1 and 1-2 was used. It is to be noted that "-" in Tables 1-1 and 1-2 denotes that the corresponding component was not used.

TABLE 1-1

| | Radiation-sensitive composition | (A) Polymer type | parts by mass | (B) Acid generating agent type | parts by mass | (C) Compound type | parts by mass | Nitrogen-containing compound type | parts by mass | Fluorine atom-containing polymer type | parts by mass | Solvent type | parts by mass |
|---|---|---|---|---|---|---|---|---|---|---|---|---|---|
| Example 1 | S-1 | A-1 | 100 | B-1 | 12.1 | C-1 | 5.0 | — | — | F-1 | 3.0 | E-1/E-2/E-3 | 1,870/800/30 |
| Example 2 | S-2 | A-1 | 100 | B-1 | 12.1 | C-2 | 6.2 | — | — | F-1 | 3.0 | E-1/E-2/E-3 | 1,870/800/30 |
| Example 3 | S-3 | A-1 | 100 | B-1 | 12.1 | C-3 | 5.8 | — | — | F-1 | 3.0 | E-1/E-2/E-3 | 1,870/800/30 |
| Example 4 | S-4 | A-1 | 100 | B-1 | 12.1 | C-4 | 5.8 | — | — | F-1 | 3.0 | E-1/E-2/E-3 | 1,870/800/30 |
| Example 5 | S-5 | A-1 | 100 | B-1 | 12.1 | C-5 | 6.8 | — | — | F-1 | 3.0 | E-1/E-2/E-3 | 1,870/800/30 |
| Example 6 | S-6 | A-2 | 100 | B-1 | 12.1 | C-1 | 5.0 | — | — | F-1 | 3.0 | E-1/E-2/E-3 | 1,870/800/30 |
| Example 7 | S-7 | A-2 | 100 | B-1 | 12.1 | C-2 | 6.2 | — | — | F-1 | 3.0 | E-1/E-2/E-3 | 1,870/800/30 |
| Example 8 | S-8 | A-2 | 100 | B-1 | 12.1 | C-3 | 5.8 | — | — | F-1 | 3.0 | E-1/E-2/E-3 | 1,870/800/30 |
| Example 9 | S-9 | A-2 | 100 | B-1 | 12.1 | C-4 | 5.8 | — | — | F-1 | 3.0 | E-1/E-2/E-3 | 1,870/800/30 |
| Example 10 | S-10 | A-2 | 100 | B-1 | 12.1 | C-5 | 6.8 | — | — | F-1 | 3.0 | E-1/E-2/E-3 | 1,870/800/30 |
| Example 11 | S-11 | A-3 | 100 | B-1 | 12.1 | — | — | — | — | F-1 | 3.0 | E-1/E-2/E-3 | 1,870/800/30 |
| Example 12 | S-12 | A-1/A-3 | 50/50 | B-1 | 12.1 | — | — | — | — | F-1 | 3.0 | E-1/E-2/E-3 | 1,870/800/30 |
| Example 13 | S-13 | A-1 | 100 | B-1 | 12.1 | C-6 | 9.6 | — | — | F-1 | 3.0 | E-1/E-2/E-3 | 1,870/800/30 |
| Example 14 | S-14 | A-1 | 100 | B-1 | 12.1 | C-7 | 11.0 | — | — | F-1 | 3.0 | E-1/E-2/E-3 | 1,870/800/30 |

TABLE 1-2

| | Radiation-sensitive composition | (A) Polymer type | parts by mass | (B) Acid generating agent type | parts by mass | (C) Compound type | parts by mass | Nitrogen-containing compound type | parts by mass | Fluorine atom-polymer type | parts by mass | Solvent type | parts by mass |
|---|---|---|---|---|---|---|---|---|---|---|---|---|---|
| Example 15 | S-15 | A-1 | 100 | B-1 | 12.1 | C-2 | 6.2 | — | — | F-2 | 3.0 | E-1/E-2/E-3 | 1,870/800/30 |
| Example 16 | S-16 | A-3 | 100 | B-1 | 12.1 | — | — | — | — | F-2 | 3.0 | E-1/E-2/E-3 | 1,870/800/30 |
| Example 17 | S-17 | A-4 | 100 | B-1 | 12.1 | C-1 | 5.0 | — | — | F-1 | 3.0 | E-1/E-2/E-3 | 1,870/800/30 |

TABLE 1-2-continued

| Radiation-sensitive composition | (A) Polymer type | parts by mass | (B) Acid generating agent type | parts by mass | (C) Compound type | parts by mass | Nitrogen-containing containing compound type | parts by mass | Fluorine atom-polymer type | parts by mass | Solvent type | parts by mass |
|---|---|---|---|---|---|---|---|---|---|---|---|---|
| Example 18 | S-18 | A-4 | 100 | B-1 | 12.1 | C-2 | 6.2 | — | — | F-1 | 3.0 | E-1/E-2/E-3 | 1,870/800/30 |
| Example 19 | S-19 | A-4 | 100 | B-1 | 12.1 | C-3 | 5.8 | — | — | F-2 | 3.0 | E-1/E-2/E-3 | 1,870/800/30 |
| Example 20 | S-20 | A-4 | 100 | B-1 | 12.1 | C-4 | 5.8 | — | — | F-1 | 3.0 | E-1/E-2/E-3 | 1,870/800/30 |
| Example 21 | S-21 | A-4 | 100 | B-1 | 12.1 | C-5 | 6.8 | — | — | F-1 | 3.0 | E-1/E-2/E-3 | 1,870/800/30 |
| Comparative Example 1 | CS-1 | A-1 | 100 | B-1 | 12.1 | — | — | D-1 | 1.4 | F-1 | 3.0 | E-1/E-2/E-3 | 1,870/800/30 |
| Comparative Example 2 | CS-2 | A-2 | 100 | B-1 | 12.1 | — | — | D-1 | 1.4 | F-1 | 3.0 | E-1/E-2/E-3 | 1,870/800/30 |

Formation of Pattern

On a silicon wafer for use as a substrate, which had been provided with an underlayer antireflective film of ARC66 (BREWER SCIENCE, Inc.) having a film thickness of 105 nm, each radiation-sensitive composition prepared in Examples and Comparative Examples was applied using CLEAN TRACK ACT12 (Tokyo Electron Limited) by spin coating. Prebaking (PB) was carried out on a hot plate at 80° C. for 60 sec to provide a resist film having a film thickness of 0.10 μm. The resist film thus provided was subjected to reduced projection exposure through a mask pattern and liquid immersion water using an ArF Immersion Scanner (S610C, Nikon Corporation; numerical aperture: 1.30). Next, post exposure baking (PEB) was carried out at the baking temperature shown in Tables 2-1 and 2-2 for 60 sec, followed by development with butyl acetate at 23° C. for 30 sec. Then, a rinse treatment was carried out with 4-methyl-2-pentanol for 10 sec, followed by drying to form a negative type resist pattern. In addition, a pattern was formed in a similar manner using methyl n-pentyl ketone, isoamyl acetate and methyl ethyl ketone as other developer solutions. It is to be noted that an exposure dose at which a hole having a diameter of 0.055 μm was formed on the wafer after the reduction projection was defined as an optimal exposure dose, and the optimal exposure dose was determined as sensitivity (mJ/cm²). The sensitivity is shown in Tables 2-1 and 2-2.

Evaluations

The following each evaluation was made on the resist patterns thus formed. The results are shown in Tables 2-1 and 2-2.

Evaluation of Resolution

Reduction projection exposure was carried out through liquid immersion water using a dot pattern that gave a pattern having a diameter of 0.055 μm after reduced projection exposure, and the minimum dimension of the hole obtained as the exposure dose increases was measured. When the minimum dimension of the hole was no greater than 0.040 μm, the evaluation was made as "favorable", whereas when the minimum dimension exceeded 0.040 μm, the evaluation was made as "unfavorable".

Evaluation of Roughness

On a silicon wafer for use as a substrate, which had been provided with an underlayer antireflective film of ARC66 (BREWER SIENCE, Inc.) having a film thickness of 105 nm, each radiation-sensitive composition prepared in Examples and Comparative Examples was applied using CLEAN TRACK ACT12 (Tokyo Electron Limited) by spin coating. PB was carried out on a hot plate at 80° C. for 60 sec to provide a resist film having a film thickness of 0.10 μm. The entire surface of the resist film thus provided was exposed at an exposure dose presented as sensitivity shown in Tables 2-1 and 2-2 using an ArF Immersion Scanner (S610C, Nikon Corporation; numerical aperture: 1.30). Post exposure baking (PEB) was then carried out at the baking temperature shown in Tables 2-1 and 2-2 for 60 sec, followed by development with butyl acetate at 23° C. for 30 sec. Then, a rinse treatment was carried out with 4-methyl-2-pentanol for 10 sec, followed by drying to form a resist film. Roughness of the surface of the resultant resist film was measured by an atomic force microscope (40×40 μm), and root-mean-square (RMS) of the surface roughness was determined. The value (nm) thus was defined as roughness, which was employed for the evaluation. When the roughness was less than 10 nm, the evaluation was made as "favorable", whereas when the roughness was no less than 10 nm, the evaluation was made as "unfavorable".

Evaluation of Missing Contact Hole

A 0.055 μm hole pattern formed at the exposure dose presented as sensitivity shown in Tables 2-1 and 2-2 was observed by a scanning electron microscope (SEM) for line-width measurement (Hitachi, Ltd., CG4000). When pattern opening of the hole was observed at all nine points in the view, the evaluation was made as "favorable", whereas when failure in pattern opening of the hole was observed at one or more points, the evaluation was made as "unfavorable".

Evaluation of Circularity

The 0.055 μm hole pattern formed through the resist coating film on the substrate at the optimum exposure dose presented as sensitivity shown in Tables 2-1 and 2-2 was observed from above using SEM for line-width measurement (Hitachi High-Technologies Corporation, CG4000). The diameter was measured at arbitrary points, and a variation 3σ was evaluated. When the variation 3σ was no greater than 0.005 μm, the evaluation was made as "favorable", whereas when the variation 3σ exceeded 0.005 μm, the evaluation was made as "unfavorable".

Evaluation of Cross-Sectional Shape

A cross-sectional shape of the 0.055 μm hole pattern formed through the resist coating film on the substrate at the optimum exposure dose presented as sensitivity shown in Tables 2-1 and 2-2 was observed (Hitachi High-Technologies Corporation, S-4800). A hole width Lb at the midpoint of the resist pattern, and a hole width La at the top of the film were measured to determine a value of (La/Lb). When the (La/Lb) value was no less than 0.9 and no greater than 1.1, the evaluation was made as "favorable", whereas when the (La/Lb) value did not fall within the above, the evaluation was made as "unfavorable".

TABLE 2-1

|  | Radiation-sensitive composition | PB Temperature (° C.) | time (sec) | PEB Temperature (° C.) | time (sec) | Sensitivity (mJ/cm²) | Resolution (μm) | Roughness (nm) | Missing contact hole | Circularity (μm) | Cross-sectional shape |
|---|---|---|---|---|---|---|---|---|---|---|---|
| Example 1 | S-1 | 80 | 60 | 105 | 60 | 20 | 0.035 | 7 | favorable | 0.0034 | favorable |
| Example 2 | S-2 | 80 | 60 | 105 | 60 | 21 | 0.035 | 8 | favorable | 0.0033 | favorable |
| Example 3 | S-3 | 80 | 60 | 105 | 60 | 20 | 0.035 | 7 | favorable | 0.0033 | favorable |
| Example 4 | S-4 | 80 | 60 | 105 | 60 | 19 | 0.035 | 7 | favorable | 0.0034 | favorable |
| Example 5 | S-5 | 80 | 60 | 105 | 60 | 20 | 0.035 | 8 | favorable | 0.0033 | favorable |
| Example 6 | S-6 | 80 | 60 | 85 | 60 | 20 | 0.035 | 8 | favorable | 0.0037 | favorable |
| Example 7 | S-7 | 80 | 60 | 85 | 60 | 21 | 0.035 | 9 | favorable | 0.0038 | favorable |
| Example 8 | S-8 | 80 | 60 | 85 | 60 | 20 | 0.035 | 8 | favorable | 0.0039 | favorable |
| Example 9 | S-9 | 80 | 60 | 85 | 60 | 19 | 0.035 | 8 | favorable | 0.0038 | favorable |
| Example 10 | S-10 | 80 | 60 | 85 | 60 | 20 | 0.035 | 9 | favorable | 0.0036 | favorable |
| Example 11 | S-11 | 80 | 60 | 105 | 60 | 15 | 0.035 | 8 | favorable | 0.0037 | favorable |
| Example 12 | S-12 | 80 | 60 | 105 | 60 | 18 | 0.035 | 9 | favorable | 0.0038 | favorable |
| Example 13 | S-13 | 80 | 60 | 105 | 60 | 18 | 0.035 | 6 | favorable | 0.0032 | favorable |
| Example 14 | S-14 | 80 | 60 | 105 | 60 | 17 | 0.035 | 5 | favorable | 0.0030 | favorable |
| Example 15 | S-15 | 80 | 60 | 105 | 60 | 21 | 0.035 | 8 | favorable | 0.0033 | favorable |

TABLE 2-2

|  | Radiation-sensitive composition | PB Temperature (° C.) | time (sec) | PEB Temperature (° C.) | time (sec) | Sensitivity (mJ/cm²) | Resolution (μm) | Roughness (nm) | Missing contact hole | Circularity (μm) | Cross-sectional shape |
|---|---|---|---|---|---|---|---|---|---|---|---|
| Example 16 | S-16 | 80 | 60 | 105 | 60 | 15 | 0.035 | 8 | favorable | 0.0037 | favorable |
| Example 17 | S-17 | 80 | 60 | 105 | 60 | 19 | 0.035 | 8 | favorable | 0.0042 | favorable |
| Example 18 | S-18 | 80 | 60 | 105 | 60 | 20 | 0.035 | 9 | favorable | 0.0043 | favorable |
| Example 19 | S-19 | 80 | 60 | 105 | 60 | 19 | 0.035 | 9 | favorable | 0.0042 | favorable |
| Example 20 | S-20 | 80 | 60 | 105 | 60 | 20 | 0.035 | 8 | favorable | 0.0045 | favorable |
| Example 21 | S-21 | 80 | 60 | 105 | 60 | 20 | 0.035 | 9 | favorable | 0.0044 | favorable |
| Comparative Example 1 | CS-1 | 80 | 60 | 105 | 60 | 25 | 0.050 | 11 | unfavorable | 0.0068 | unfavorable |
| Comparative Example 2 | CS-2 | 80 | 60 | 85 | 60 | 27 | 0.050 | 12 | unfavorable | 0.0066 | unfavorable |

As is clear from Tables 2-1 and 2-2, generation of roughness of the surface of light-exposed sites and missing contact hole after development can be suppressed, and a pattern that is superior in lithography characteristics such as resolution and circularity is obtained according to the pattern-forming method of the embodiment of the present invention. It is to be noted that an achievement of similar effects was ascertained also on a pattern formed using methyl n-pentyl ketone, isoamyl acetate or methyl ethyl ketone as a developer solution.

According to the embodiment of the present invention, a pattern-forming method that suppresses generation of roughness of the surface of light-exposed sites and missing contact hole after development and that attains superior in lithography characteristics such as resolution and circularity, and a radiation-sensitive composition suited for the pattern-forming method can be also provided. Therefore, the embodiment of the present invention is suited for microfabrication by way of lithography.

Obviously, numerous modifications and variations of the present invention are possible in light of the above teachings. It is therefore to be understood that within the scope of the appended claims, the invention may be practiced otherwise than as specifically described herein.

The invention claimed is:
1. A pattern-forming method comprising:
providing a resist film on a substrate using a radiation-sensitive composition;
exposing the resist film; and
developing the exposed resist film using a developer solution which comprises no less than 80% by mass of an organic solvent,
wherein the radiation-sensitive composition comprises:
a first polymer that comprises a structural unit comprising an acid-labile group;
a radiation-sensitive acid generator; and
a non-polymeric compound other than the radiation-sensitive acid generator,
the non-polymeric compound being represented by formula (2):

$$R^1\text{-}A^-X^+ \qquad (2)$$

wherein, in the formula (2),
$R^1$ represents a hydrogen atom or a monovalent organic group;
$A^-$ represents $-N^-\text{---}SO_2\text{---}R^D$, $-COO^-$, $-O^-$ or $-SO_3^-$, wherein in a case where $A^-$ represents $-SO_3^-$, $-SO_3^-$ does not directly bond to a carbon atom which bonds to a fluorine atom;

$R^D$ represents a linear or branched monovalent hydrocarbon group having 1 to 10 carbon atoms or a cyclic monovalent hydrocarbon group having 3 to 20 carbon atoms, wherein a part or all of hydrogen atoms of the hydrocarbon group represented by $R^D$ may be substituted by a fluorine atom; and $X^+$ represents an onium cation, wherein the non-polymeric compound generates an acid upon exposure, and the acid is weaker than an acid generated by the radiation-sensetive acid generator.

2. The pattern-forming method according to claim 1, wherein the first polymer further comprises a structural unit derived from a compound represented by formula (3-1), a structural unit derived from a compound represented by formula (3-2) or a combination thereof:

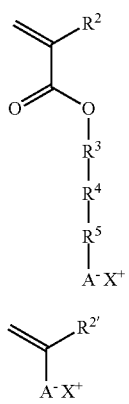

(3-1)

(3-2)

wherein, in the formula (3-1), $A^-$ and $X^+$ are as defined in the formula (2);

$R^2$ represents a hydrogen atom, a methyl group or a trifluoromethyl group;

$R^3$ and $R^5$ each independently represent a single bond, a linear or branched divalent hydrocarbon group having 1 to 10 carbon atoms, or a divalent hydrocarbon group that comprises a cyclic structure and has 3 to 20 carbon atoms, wherein a part or all of hydrogen atoms of the linear or branched divalent hydrocarbon group and the divalent hydrocarbon group represented by $R^3$ and $R^5$ may be substituted by a fluorine atom; and $R^4$ represents a single bond, —O—, —C(=O)—, —C(=O)—O—, —O—C(=O)— or a sulfinyl group, and in the formula (3-2), $A^-$ and $X^+$ are as defined in the formula (2); and $R^{2'}$ represents a hydrogen atom, a methyl group or a trifluoromethyl group.

3. The pattern-forming method according to claim 2, wherein the radiation-sensitive composition further comprises a second polymer that comprises the structural unit derived from the compound represented by the formula (3-1), the structural unit derived from the compound represented by the formula (3-2), or a combination thereof.

4. The pattern-forming method according to claim 1, wherein $X^+$ is represented by formula (4):

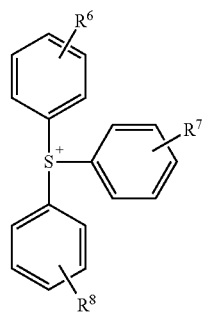

(4)

wherein, in the formula (4), $R^6$ to $R^8$ each independently represent a hydrogen atom, a halogen atom, a hydroxyl group, a substituted or unsubstituted alkyl group having 1 to 10 carbon atoms, a substituted or unsubstituted cycloalkyl group having 3 to 12 carbon atoms, or a substituted or unsubstituted alkoxy group having 1 to 10 carbon atoms.

5. The pattern-forming method according to claim 1, wherein the radiation-sensitive composition further comprises a second polymer that comprises a structural unit derived from the compound represented by formula (3-1), a structural unit derived from the compound represented by formula (3-2), or a combination thereof:

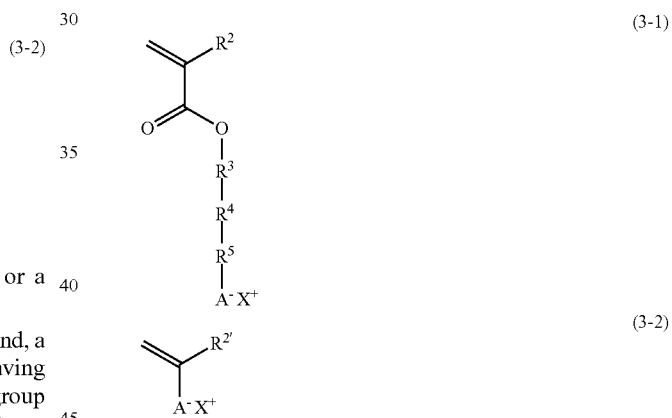

(3-1)

(3-2)

wherein, in the formula (3-1), $A^-$ and $X^+$ are as defined in the formula (2);

$R^2$ represents a hydrogen atom, a methyl group or a trifluoromethyl group;

$R^3$ and $R^5$ each independently represent a single bond, a linear or branched divalent hydrocarbon group having 1 to 10 carbon atoms, or a divalent hydrocarbon group that comprises a cyclic structure and has 3 to 20 carbon atoms, wherein a part or all of hydrogen atoms of the linear or branched divalent hydrocarbon group and the divalent hydrocarbon group represented by $R^3$ and $R^5$ may be substituted by a fluorine atom; and $R^4$ represents a single bond, —O—, —C(=O)—, —C(=O)—O—, —O—C(=O)— or a sulfinyl group, and in the formula (3-2), $A^-$ and $X^+$ are as defined in the formula (2); and $R^{2'}$ represents a hydrogen atom, a methyl group or a trifluoromethyl group.

6. The pattern-forming method according to claim 1, wherein the radiation-sensitive acid generator is other than the first polymer.

7. The pattern-forming method according to claim 1, wherein $A^-$ bonds to a carbon atom and the carbon atom does not have an electron-withdrawn group or an electron-withdrawn atom.

8. The pattern-forming method according to claim 1, wherein $A^-$ represents $-SO_3^-$.

9. The pattern-forming method according to claim 1, wherein, in the formula (2), $R^1$ represents a hydrogen atom, a substituted or unsubstituted alkyl group having 1 to 20 carbon atoms, a substituted or unsubstituted cycloalkyl group having 3 to 20 carbon atoms, a substituted or unsubstituted aryl group having 6 to 30 carbon atoms, a substituted or unsubstituted aralkyl group having 7 to 30 carbon atoms, or a heterocyclic group having 3 to 30 carbon atoms.

10. A radiation-sensitive composition comprising:
a first polymer that comprises a structural unit comprising acid-labile group;
a radiation-sensitive acid generator; and
a non-polymeric compound other than the radiation-sensitive acid generator, the non-polymeric compound being represented by formula (2), $$R^1\text{-}A^-X^+ \quad (2)$$

wherein, in the formula (2),
$R^1$ represents a hydrogen atom or a monovalent organic group;
$A^-$ represents $-N^-\text{---}SO_2\text{---}R^D$, $-COO^-$, $-O^-$ or $-SO_3^-$, wherein in a case where $A^-$ represents $-SO_3^-$, $-SO_3^-$ does not directly bond to a carbon atom which bond to a fluorine atom;
$R^D$ represents a linear or branched monovalent hydrocarbon group having 1 to 10 carbon atoms or a cyclic monovalent hydrocarbon group having 3 to 20 carbon atoms, wherein a part or all of hydrogen atoms of the hydrocarbon group represented by $R^D$ may be substituted by a fluorine atom; and
$X^+$ represents an onium cation,
wherein the non-polymeric compound generates an acid upon exposure, and the acid is weaker than an acid generated by the radiation-sensitive acid generator.

11. The radiation-sensitive composition according to claim 10, wherein the first polymer further comprises a structural unit derived from a compound represented by formula (3-1), a structural unit derived from a compound represented by formula (3-2) or a combination thereof:

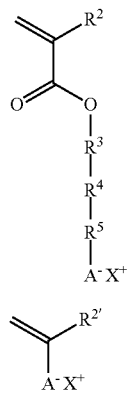

(3-1)

(3-2)

wherein, in the formula (3-1),
$A^-$ and $X^+$ are as defined in the formula (2);
$R^2$ represents a hydrogen atom, a methyl group or a trifluoromethyl group;
$R^3$ and $R^5$ each independently represent a single bond, a linear or branched divalent hydrocarbon group having 1 to 10 carbon atoms, or a divalent hydrocarbon group that comprises a cyclic structure and has 3 to 20 carbon atoms, wherein a part or all of hydrogen atoms of the linear or branched divalent hydrocarbon group and the divalent hydrocarbon group represented by $R^3$ and $R^5$ may be substituted by a fluorine atom; and $R^4$ represents a single bond, $-O-$, $-C(=O)-$, $-C(=O)-O-$, $-O-C(=O)-$ or a sulfinyl group, and in the formula (3-2),
$A^-$ and $X^+$ are as defined in the formula (2); and
$R^{2\prime}$ represents a hydrogen atom, a methyl group or a trifluoromethyl group.

12. The radiation-sensitive composition according to claim 11, wherein the radiation-sensitive composition further comprises a second polymer that comprises the structural unit derived from the compound represented by the formula (3-1), the structural unit derived from the compound represented by the formula (3-2), or a combination thereof.

13. The radiation-sensitive composition according to claim 10, wherein $X^+$ is represented by formula (4):

(4)

wherein, in the formula (4), $R^6$ to $R^8$ each independently represent a hydrogen atom, a halogen atom, a hydroxyl group, a substituted or unsubstituted alkyl group having 1 to 10 carbon atoms, a substituted or unsubstituted cycloalkyl group having 3 to 12 carbon atoms, or a substituted or unsubstituted alkoxy group having 1 to 10 carbon atoms.

14. The radiation-sensitive composition according to claim 10, wherein the radiation-sensitive composition further comprises a second polymer that comprises a structural unit derived from the compound represented by formula (3-1), a structural unit derived from the compound represented by formula (3-2), or a combination thereof, (3-1)

(3-2)

wherein, in the formula (3-1),
A⁻ and X⁺ are as defined in the formula (2);
R² represents a hydrogen atom, a methyl group or a trifluoromethyl group;
R³ and R⁵ each independently represent a single bond, a linear or branched divalent hydrocarbon group having 1 to 10 carbon atoms, or a divalent hydrocarbon group that comprises a cyclic structure and has 3 to 20 carbon atoms, wherein a part or all of hydrogen atoms of the linear or branched divalent hydrocarbon group and the divalent hydrocarbon group represented by R³ and R⁵ may be substituted by a fluorine atom; and
R⁴ represents a single bond, —O—, —C(═O)—, —C(═O)—O—, —O—C(═O)— or a sulfinyl group, and in the formula (3-2),
A" and X⁺ are as defined in the formula (2); and
R²' represents a hydrogen atom, a methyl group or a trifluoromethyl group.

15. The radiation-sensitive composition according to claim 10, wherein the radiation-sensitive acid generator is other than the first polymer.

16. The radiation-sensitive composition according to claim 10, wherein A⁻ bonds to a carbon atom and the carbon atom does not have an electron-withdrawn group or an electron-withdrawn atom.

17. The radiation-sensitive composition according to claim 10, wherein A⁻ represents —SO₃⁻.

18. The radiation-sensitive composition according to claim 10, wherein, in the formula (2), R¹ represents a hydrogen atom, a substituted or unsubstituted alkyl group having 1 to 20 carbon atoms, a substituted or unsubstituted cycloalkyl group having 3 to 20 carbon atoms, a substituted or unsubstituted aryl group having 6 to 30 carbon atoms, a substituted or unsubstituted aralkyl group having 7 to 30 carbon atoms, or a heterocyclic group having 3 to 30 carbon atoms.

* * * * *